(12) United States Patent
Caron et al.

(10) Patent No.: US 12,141,971 B2
(45) Date of Patent: Nov. 12, 2024

(54) SYSTEMS AND METHODS FOR PATIENT TUMOR-IMMUNE PHENOTYPING FROM IMMUNOFLUORESCENCE (IF) IMAGE ANALYSIS

(71) Applicant: Sanofi, Paris (FR)

(72) Inventors: Anne Caron, Antony (FR); Bema Zouakognon Coulibaly, Paris (FR); Anthony Mei, North Wales, PA (US); Reza Olfati-Saber, Wellesley, MA (US); Robert John Pomponio, Medway, MA (US); Qi Tang, Hopewell, NJ (US); Rui Wang, Belmont, MA (US)

(73) Assignee: SANOFI, Paris (FR)

( * ) Notice: Subject to any disclaimer, the term of this patent is extended or adjusted under 35 U.S.C. 154(b) by 298 days.

(21) Appl. No.: 17/722,263

(22) Filed: Apr. 15, 2022

(65) Prior Publication Data

US 2022/0335606 A1  Oct. 20, 2022

Related U.S. Application Data

(60) Provisional application No. 63/175,540, filed on Apr. 15, 2021.

(30) Foreign Application Priority Data

Sep. 8, 2021  (EP) .................................... 21315155

(51) Int. Cl.
  *G06T 7/00*  (2017.01)
  *G06T 7/62*  (2017.01)
  (Continued)

(52) U.S. Cl.
  CPC .............. *G06T 7/0012* (2013.01); *G06T 7/62* (2017.01); *G06V 20/698* (2022.01); *G16B 20/00* (2019.02); *G16H 50/50* (2018.01); *G06T 2207/10024* (2013.01); *G06T 2207/10056* (2013.01); *G06T 2207/10064* (2013.01);
  (Continued)

(58) Field of Classification Search
  USPC ......................................... 382/133
  See application file for complete search history.

(56) References Cited

U.S. PATENT DOCUMENTS 10,956,795 B2 * 3/2021 Madabhushi .... G06V 30/19173
2023/0143860 A1 * 5/2023 Li ........................ G06V 20/698
                                                  382/128

OTHER PUBLICATIONS

Echarti et al., CD8+ and Regulatory T cells Differentiate Tumor Immune Phenotypes and Predict Survival in Locally Advanced Head and Neck Cancer. Cancers (Basel). Sep. 19, 2019;11(9):1398, 13 pages.

(Continued)

*Primary Examiner* — Jacky X Zheng
(74) *Attorney, Agent, or Firm* — McCarter & English, LLP

(57) ABSTRACT

Embodiments of the present disclosure include systems, methods, and non-transitory computer-readable storage media for automated determination of a patient tumor-immune phenotype from immunofluorescence (IF) image analysis of pathology slides based on a tumor infiltrating lymphocytes score, a non-tumor infiltrating lymphocytes score, and a non-tumor infiltrating lymphocytes at tumor margin score.

21 Claims, 12 Drawing Sheets
(7 of 12 Drawing Sheet(s) Filed in Color)

(51) Int. Cl.
    *G06V 20/69*     (2022.01)
    *G16B 20/00*     (2019.01)
    *G16H 50/50*     (2018.01)

(52) U.S. Cl.
    CPC ............... *G06T 2207/20021* (2013.01); *G06T 2207/20036* (2013.01); *G06T 2207/20081* (2013.01); *G06T 2207/30024* (2013.01); *G06T 2207/30096* (2013.01); *G06V 2201/03* (2022.01)

(56) References Cited

OTHER PUBLICATIONS

Mi et al., Digital Pathology Analysis Quantifies Spatial Heterogeneity of CD3, CD4, CD8, CD20, and FoxP3 Immune Markers in Triple-Negative Breast Cancer. Front Physiol. Oct. 19, 2020;11:583333, 22 pages.

Sun et al., Expression of PD-1 and PD-L1 on Tumor-Infiltrating Lymphocytes Predicts Prognosis in Patients with Small-Cell Lung Cancer. Onco Targets Ther. Jul. 3, 2020;13:6475-6483.

Yoo et al., Whole-Slide Image Analysis Reveals Quantitative Landscape of Tumor-Immune Microenvironment in Colorectal Cancers. Clin Cancer Res. Feb. 15, 2020;26(4):870-881.

\* cited by examiner

SYSTEMS AND METHODS FOR PATIENT TUMOR-IMMUNE PHENOTYPING FROM IMMUNOFLUORESCENCE (IF) IMAGE ANALYSIS

CROSS-REFERENCE TO RELATED APPLICATIONS

The present application claims benefit of and priority to U.S. Provisional Patent Application No. 63/175,540 filed Apr. 15, 2021, and claims priority under 35 U.S.C. § 119 to European Patent Application No. 21315155.8 filed Sep. 8, 2021. The contents of each of which are incorporated by reference in their entirety.

TECHNICAL FIELD

Some embodiments of the disclosure relate to methods and systems for classifying a patient into a tumor-immune phenotype.

BACKGROUND

For the development of checkpoint inhibitors and other oncological drugs, a patient's tumor-immune phenotype is an emerging and important aspect of predicting the patient's potential response to various therapies. Examples of these tumor-immune phenotypes include immune desert, immune-excluded, and inflamed. In an immune desert phenotype, cytotoxic lymphocytes are not present in the tumor micro environment and few or no cytotoxic lymphocytes are present in the surrounding stromal area. In an immune-excluded phenotype, cytotoxic lymphocytes are present in the surrounding stromal area, although cytotoxic lymphocytes are not able to penetrate into the tumor micro environment. In an inflamed phenotype, both the tumor micro environment and the surrounding stromal area contain cytotoxic lymphocytes.

Identifying a patient's tumor-immune phenotype enables the application of a treatment strategy to target the individual immune biology, and can increase the chance that an individual responds to a specific treatment.

SUMMARY

Methods for determining a tumor-immune phenotype from one or more immunofluorescence (IF) images are provided. A method includes receiving, from one or more databases, or obtaining at least one digital microscopy image of an immunofluorescence (IF) pathology slide of a patient, in accordance with some embodiments. In some embodiments, the method also includes performing immunofluorescence imaging to obtain the at least one digital microscopy image of the immunofluorescence (IF) pathology slide of the patient. The method also includes receiving or obtaining a tissue level tumor mask, which may be based on pathologist annotation, and identifying which portion or portions of the at least one digital microscopy image correspond to one or more tumor nests. The method further includes producing a plurality of color-based channel images each corresponding to a different color-based channel in a plurality of color-based channels for each image tile in a plurality of image tiles cumulatively corresponding to the at least one digital microscopy image of the IF pathology slide. The plurality of color-based channels includes an epithelial channel including epithelial cell image data, a cell nuclei channel including cell nuclei image data, and at least one lymphocyte channel including lymphocyte image data. The method further includes, for at least some of the tiles, segmenting the epithelial cell channel image for the tile into a tumor region and a non-tumor region based on the tissue level tumor mask and the epithelial cell image data. The method also includes, for at least some of the tiles, determining a tumor margin region for the tile based on a pre-specified margin outside a boundary of the tumor region based on the tissue level tumor mask. The method further includes, for the tiles including lymphocyte image data, segmenting the lymphocyte image data to determine a location and an area for each lymphocyte within the tile. The method further includes, for at least some of the tiles, calculating a tumor infiltrating lymphocytes score (TILS) based on a total area of the lymphocytes in the tumor region and a total area of the tumor region for the tile. The method also includes, for at least some of the tiles, calculating a non-tumor infiltrating lymphocytes score (NTILS) based on a total area of the lymphocytes in the non-tumor region and a total area of the non-tumor region for the tile. The method further includes, for at least some of the tiles, calculating a non-tumor infiltrating lymphocytes at tumor margin score (NTILS_margin) based on a total area of lymphocytes in the tumor margin and a total area of the tumor margin for the tile. The method also includes aggregating tile level results from at least some of the plurality of tiles to determine one or more of: a patient level tumor infiltrating lymphocytes score, a patient level non-tumor infiltrating lymphocytes score, and a patient level non-tumor infiltrating lymphocytes at tumor margin score. The method further includes classifying the patient into a tumor-immune phenotype of a plurality of tumor-immune phenotypes including immune deserts, immune-excluded tumors, and inflamed tumors based on one or more of the patient level tumor infiltrating lymphocytes score, the patient level non-tumor infiltrating lymphocytes score, and the patient level non-tumor infiltrating lymphocytes at the tumor margin score.

In some embodiments of methods, classifying the patient into a tumor-immune phenotype of a plurality of tumor-immune phenotypes includes: comparing the patient level tumor infiltrating lymphocytes score to a first threshold; where the patient level tumor infiltrating lymphocytes score meets or exceeds the first threshold, classifying the patient into an inflamed tumor-immune phenotype; and where the patient level tumor infiltrating lymphocytes score falls below the first threshold: comparing the larger of the patient level non-tumor infiltrating lymphocytes score and the patient level non-tumor infiltrating lymphocytes at the tumor margin score to a second threshold; where the larger of the patient level non-tumor infiltrating lymphocytes score and the patient level non-tumor infiltrating lymphocytes at the tumor margin score falls below the second threshold, classifying the patient into an immune desert phenotype; and where the larger of the patient level non-tumor infiltrating lymphocytes score and the patient level non-tumor infiltrating lymphocytes at the tumor margin score meets or exceeds the second threshold, classifying the patient into an immune-excluded tumor-immune phenotype. In some embodiments, the first threshold is 0.005, or the second threshold is 0.025, or the first threshold is 0.005 and the second threshold is 0.025. In some embodiments, the first threshold, the second threshold, or both fall in a range of 0.001 to 0.5. In some embodiments, the first threshold and the second threshold are determined based on training data. In some embodiments, the first threshold and the second threshold are determined based on training data including multiple different types of cancer. In some embodiments, the first threshold and the second threshold are determined based on training data including only one type of cancer. In some embodiments, the first threshold and the second threshold are specific to a single type of cancer. In some embodiments, the first threshold and the second threshold are applicable to multiple different types of cancer.

In some embodiments of methods, producing the plurality of color-based channel images comprises dividing the at least one digital microscopy image of the IF pathology slide into a plurality of image tiles, and creating the plurality of color-based channel images for each of the plurality of image tiles from the corresponding image tile using color deconvolution.

In some embodiments of methods, producing the plurality of color-based channel images comprises creating a plurality of full image, color-based channel images from the at least one digital microscopy image using color deconvolution, and dividing each of the plurality of full image, color-based channel images into tiles to form the plurality of color-based channel images for each of the plurality of image tiles.

In some embodiments of methods, the tumor infiltrating lymphocytes score (TILS) for a tile is determined based on the total area of lymphocytes in the tumor region divided by the total area of the tumor region for the tile; the non-tumor infiltrating lymphocytes score (NTILS) for a tile is determined based the total area of lymphocytes in the non-tumor region for the tile divided by the total area of the non-tumor region for the tile; and the non-tumor infiltrating lymphocytes at tumor margin score (NTILS_margin) for a tile is determined based the total area of lymphocytes in the tumor margin that is divided by the total area of the tumor margin for the tile.

In some embodiments of methods, the at least one lymphocyte channel includes cytotoxic lymphocyte image data. In some embodiments of methods, the at least one lymphocyte channel includes CD8+ T cell image data. In some embodiments of methods, the at least one lymphocyte channel includes CD3+ T cell image data. In some embodiments of methods, the at least one lymphocyte channel includes natural killer (NK) cytotoxic lymphocyte image data. In some embodiments of methods, the at least one lymphocyte channel includes one or more of CD8+ T cell image data, CD3+ T cell image data, and natural killer (NK) cytotoxic lymphocyte image data.

In some embodiments of methods, the epithelial cell channel includes pan cytokeratin (pan-CK) stained marker image data.

In some embodiments of methods, the cell nuclei channel includes 4',6-diamidino-2-phenylindole (DAPI) stained marker image data.

In some embodiments of methods, aggregating the tile level results includes: aggregating tumor infiltrating lymphocytes scores for all the tiles of the plurality of tiles; aggregating non-tumor infiltrating lymphocytes scores for all the tiles of the plurality of tiles; and aggregating non-tumor infiltrating lymphocytes at tumor margin scores for all the tiles of the plurality of tiles.

Some embodiments of methods further comprise, prior to dividing the digital microcopy image of the IF pathology slide into a plurality of image tiles, performing global thresholding on the digital microscopy image to separate signal from background noise.

In some embodiments of methods, for at least some of the plurality color-based channel images for at least some of the plurality of tiles, the method further comprises employing at least one image morphology filter to correct the color-based channel images. In some embodiments of methods, the at least one image morphology filter includes correcting out-of-focus regions and removing staining artifacts in the color-based channel images. In some embodiments of methods, a top-hat filtering morphology operation is employed to correct the out-of-focus regions and remove the staining artifacts. In some embodiments of methods, the at least one image morphology filter includes removing small artifacts in the color-based channel images. In some embodiments of methods, an opening filtering morphology operation is employed to remove the small artifacts in the images of the color-based channels. In some embodiments of methods, the at least one image morphology filter includes filling small holes for the epithelial cell image data and the cell nuclei image data. In some embodiments of methods, a closing filtering morphology operation is employed to fill the small holes for epithelial cell image data and the cell nuclei image data.

In some embodiments of methods, a watershed image morphology operation is employed to segment the lymphocyte image data to determine a location and an area for each lymphocyte within each tile including lymphocytes.

Some embodiments of methods further include: 1) for each tile: determining a total area of cell nuclei for the tile; determining the total area of tumor region for the tile; determining the total area of lymphocytes in the tumor region for the tile; determining the total area of non-tumor region for the tile; determining the total area of lymphocytes in the non-tumor region for the tile; determining the total area of tumor margin for the tile; and determining the total area of nuclei in the tumor margin for the tile; 2) determining whether a tile is included in the aggregated tile results for the patient level tumor infiltrating lymphocytes score based on whether the total area of cell nuclei for the tile meets a TILS minimum nuclei threshold and based on whether the total tumor region area meets a minimum tumor area threshold; 3) determining whether the tile is included in the aggregated tile results for the patient level non-tumor infiltrating lymphocytes score based on whether the total area of cell nuclei for the tile meets an NTILS minimum nuclei threshold and based on whether the total non-tumor region area meets a minimum non-tumor area threshold; and 4) determining whether the tile is included in the aggregated tile results for the patient level non-tumor infiltrating lymphocytes at tumor margin score based on whether the total tumor margin area meets minimum tumor margin area threshold and based on the total area of cell nuclei in the tumor margin for the tile meets a minimum tumor margin nuclei threshold.

In some embodiments of the method, the patient level tumor infiltrating lymphocytes score is the median of the tile level tumor infiltrating lymphocytes scores for the tiles included in the aggregated tile level results for the tumor infiltrating lymphocytes score; the patient level non-tumor infiltrating lymphocytes score is the median of the tile level non-tumor infiltrating lymphocytes scores for the tiles included in the aggregated tile level results for the non-tumor infiltrating lymphocytes score; and the patient level non-tumor infiltrating lymphocytes at the tumor margin score is the median of the tile level non-tumor infiltrating lymphocytes at the tumor margin scores for the tiles included in the aggregated tile level results for the non-tumor infiltrating lymphocytes at the tumor margin score.

Some embodiments of methods also include digitalizing at least one microscopy image of an IF pathology slide of the patient and storing the resulting at least one digital microscopy image of the IF pathology slide of the patient in the one or more databases.

Some embodiments of methods also include transmitting the tumor-immune phenotype classification of the patient to a user computing device with a computer display.

Some embodiments of methods also include transmitting the tumor-immune phenotype classification of the patient to a user computing device with a computer display. Some embodiments of methods also include displaying the tumor-immune phenotype classification of the patient on the computer display. Some embodiments of methods also include storing the tumor-immune phenotype classification of the patient within the one or more databases.

Some embodiments of methods also include providing a recommendation of a type of treatment or a category of treatment based on the tumor-immune phenotype classification of the patient.

In some embodiments of the methods, parallel graphics processing units (GPUs) are used to perform GPU parallel image morphology operations.

In some embodiments, the method also includes obtaining the at least one digital microscopy image of an immunofluorescence (IF) pathology slide of a patient. In some embodiments, the method also includes performing immunofluorescence imaging to obtain the at least one digital microscopy image of the immunofluorescence (IF) pathology slide of the patient.

Non-transitory, computer-readable media storing one or more instructions executable by a computer system are provided. When executed, the one or more instructions perform any of the methods described or claimed herein in accordance with various embodiments. In accordance with an embodiment, when executed, the one or more instructions perform operations including receiving, from one or more databases, at least one digital microscopy image of an immunofluorescence (IF) pathology slide of a patient. The one or more instructions further perform operations including receiving or obtaining a tissue level tumor mask identifying which portion or portions of the digital microscopy image correspond to one or more tumor nests. The one or more instructions further perform operations including producing a plurality of color-based channel images each corresponding to a different color-based channel in a plurality of color-based channels for each image tile in a plurality of image tiles cumulatively corresponding to the at least one digital microscopy image of the IF pathology slide. The plurality of color-based channels includes an epithelial cell channel including epithelial cell image data, a cell nuclei channel including cell nuclei image data, and at least one lymphocyte channel including lymphocyte image data. The one or more instructions also perform operations including, for at least some of the tiles, segmenting the epithelial cell image data for the tile into a tumor region and a non-tumor region based on the tissue level tumor mask, and the epithelial cell image data. The one or more instructions further perform operations including, for at least some of the tiles, determining a tumor margin region for the tile based on a pre-specified margin outside a boundary of the tumor region based on the tissue level tumor mask. The one or more instructions also perform operations including, for the tiles including lymphocyte image data, determining a location and an area for each lymphocyte within the tile. The one or more instructions also perform operations including, for at least some of the tiles, calculating a tumor infiltrating lymphocytes score (TILS) based on a total area of the lymphocytes in the tumor region and a total area of the tumor region for the tile. The one or more instructions further perform operations including, for at least some of the tiles, calculating a non-tumor infiltrating lymphocytes score (NTILS) based on a total area of the lymphocytes in the non-tumor region and a total area of the non-tumor region for the tile. The one or more instructions also perform operations including, for at least some of the tiles, calculating a non-tumor infiltrating lymphocytes at tumor margin score (NTILS_Margin) based on a total area of lymphocytes in the tumor margin and a total area of the tumor margin for the tile. The one or more instructions further perform operations including aggregating tile level results from at least some of the plurality of tiles to determine a patient level tumor infiltrating lymphocytes score, a patient level non-tumor infiltrating lymphocytes score, and a patient level non-tumor infiltrating lymphocytes at tumor margin score. The one or more instructions also perform operations including classifying the patient into a tumor-immune phenotype of a plurality of tumor-immune phenotypes including immune deserts, immune-excluded tumors and inflamed tumors based on the patient level tumor infiltrating lymphocytes score, the patient level non-tumor infiltrating lymphocytes score, and the patient level non-tumor infiltrating lymphocytes at the tumor margin score.

Systems for determining a tumor-immune phenotype from one or more immunofluorescence (IF) images of a patient are provided in accordance with some embodiments. A system includes one or more databases and one or more processors in accordance with some embodiments. The one or more processors are configured to receive, from the one or more databases, at least one digital microscopy image of an immunofluorescence (IF) pathology slide of a patient. The one or more processors are also configured to receive or obtain a tissue level tumor mask, which may be based on pathologist annotation, identifying which portion or portions of the digital microscopy image correspond to one or more tumor nests. The one or more processors are also configured to produce a plurality of color-based channel images each corresponding to a different color-based channel in a plurality of color-based channels for each image tile in a plurality of image tiles cumulatively corresponding to the at least one digital microscopy image of the IF pathology slide. The plurality of color-based channels includes an epithelial channel including epithelial cell image data, a nuclei channel including nuclei image data, and at least one lymphocyte channel including lymphocyte image data. The one or more processors are further configured to, for at least some of the tiles, segment the epithelial channel image for the tile into a tumor region and a non-tumor region based on the tissue level tumor mask, and the epithelial cell image data. The one or more processors are also configured to, for at least some of the tiles, determine a tumor margin region for the tile based on a pre-specified margin outside a boundary of the tumor region based on the tissue level tumor mask. The one or more processors are further configured to, for the tiles including lymphocyte image data, determine a location and an area for each lymphocyte within the tile. The one or more processors are further configured to, for at least some of the tiles, calculate a non-tumor infiltrating lymphocytes score (NTILS) based on a total area of the lymphocytes in the non-tumor region and a total area of the non-tumor region for the tile. The one or more processors are also configured to, for at least some of the tiles, calculate a non-tumor infiltrating lymphocytes score (NTILS) based on a total area of the lymphocytes in the non-tumor region and a total area of the non-tumor region for the tile. The one or more processors are further configured to, for at least some of the tiles, calculate a non-tumor infiltrating lymphocytes at tumor margin score (NTILS_Margin) based on a total area of lymphocytes in the tumor margin and a total area of the tumor margin for the tile. The one or more processors are also configured to aggregate tile level results from at least some of the plurality of tiles to determine a patient level tumor infiltrating lymphocytes score, a patient level non-tumor infiltrating lymphocytes score, and a patient level non-tumor infiltrating lymphocytes at tumor margin score. The one or more processors are further configured to classify the patient into a tumor-immune phenotype of a plurality of tumor-immune phenotypes including immune deserts, immune-excluded tumors and inflamed tumors based on the patient level tumor infiltrating lymphocytes score, the patient level non-tumor infiltrating lymphocytes score, and the patient level non-tumor infiltrating lymphocytes at the tumor margin score.

In some embodiments, the one or more processors are configured to classify the patient into a tumor-immune phenotype of a plurality of tumor-immune phenotypes by: comparing the patient level tumor infiltrating lymphocytes score to a first threshold; where the patient level tumor infiltrating lymphocytes score meets or exceeds the first threshold, classifying the patient into an inflamed tumor-immune phenotype; and where the patient level tumor infiltrating lymphocytes score falls below the first threshold: comparing the larger of the patient level non-tumor infiltrating lymphocytes score and the patient level non-tumor infiltrating lymphocytes at the tumor margin score to a second threshold; where the larger of the patient level non-tumor infiltrating lymphocytes score and the patient level non-tumor infiltrating lymphocytes at the tumor margin score falls below the second threshold, classifying the patient into an immune desert phenotype; and where the larger of the patient level non-tumor infiltrating lymphocytes score and the patient level non-tumor infiltrating lymphocytes at the tumor margin score meets or exceeds the second threshold, classifying the patient into an immune-excluded tumor-immune phenotype.

In some embodiments of a system, the first threshold is 0.005, or the second threshold is 0.025, or the first the first threshold is 0.005 and the second threshold is 0.002. In some embodiments, the first threshold, the second threshold, or both fall in a range of 0.001 to 0.5. In some embodiments, the first threshold and the second threshold are determined based on training data. In some embodiments, the first threshold and the second threshold are determined based on training data including multiple different types of cancer. In some embodiments, the first threshold and the second threshold are determined based on training data including only one type of cancer. In some embodiments, the first threshold and the second threshold are specific to a single type of cancer. In some embodiments, the first threshold and the second threshold are applicable to multiple different types of cancer.

In some embodiments of a system, the plurality of color-based channel images includes dividing the at least one digital microscopy image of the IF pathology slide into a plurality of image tiles, and creating the plurality of color-based channel images for each of the plurality of image tiles from the corresponding image tile using color deconvolution. In some embodiments, producing the plurality of color-based channel images comprises creating a plurality of full image, color-based, channel images from the at least one digital microscopy image using color deconvolution, and dividing each of the plurality of full image, color-based channel images into tiles to form the plurality of color-based channel images for each of the plurality of image tiles.

In some embodiments of a system, the instructions executed on the one or more processors are configured to: determine the tumor infiltrating lymphocytes score (TILS) for a tile based on the total area of lymphocytes in the tumor region divided by the total area of the tumor region for the tile; determine the non-tumor infiltrating lymphocytes score (NTILS) for a tile based the total area of lymphocytes in the non-tumor region for the tile divided by the total area of the non-tumor region for the tile; and determine the non-tumor infiltrating lymphocytes at tumor margin score (NTILS_margin) for a tile based the total area of lymphocytes in the tumor margin that is divided by the total area of the tumor margin for the tile.

In some embodiments of a system, the at least one lymphocyte channel includes cytotoxic lymphocyte image data. In some embodiments, the at least one lymphocyte channel includes CD8+ T cell image data. In some embodiments, the at least one lymphocyte channel includes CD3+ T cell image data. In some embodiments, the at least one lymphocyte channel includes natural killer (NK) cytotoxic lymphocyte image data. In some embodiments, the at least one lymphocyte channel includes one or more of CD8+ T cell image data, CD3+ T cell image data, and natural killer (NK) cytotoxic lymphocyte image data. In some embodiments, the epithelial cell channel includes pan cytokeratin (pan-CK) stained marker image data. In some embodiments, the cell nuclei channel includes 4',6-diamidino-2-phenylindole (DAPI) stained marker image data. In some embodiments, aggregating the tile level results includes: 1) aggregating tumor infiltrating lymphocytes scores for all the tiles of the plurality of tiles; 2) aggregating non-tumor infiltrating lymphocytes scores for all the tiles of the plurality of tiles; and 3) aggregating non-tumor infiltrating lymphocytes at tumor margin scores for all the tiles of the plurality of tiles.

In some embodiments of systems, prior to dividing the digital microcopy image of the IF pathology slide into a plurality of image tiles, the instructions executed on the one or more processors are further configured to perform global thresholding on the digital microscopy image to separate signal from background noise for each color-based channel.

In some embodiments of systems, for at least some of the plurality color-based channel images for at least some of the plurality of tiles, the instructions executed on the one or more processors are further configured to employ at least one image morphology filter to correct the color-based channel images. In some embodiments, the at least one image morphology filter includes correcting out-of-focus regions and removing staining artifacts in the color-based channel images. In some embodiments, a top-hat filtering morphology operation is employed to correct the out-of-focus regions and remove the staining artifacts. In some embodiments, the at least one image morphology filter includes removing small artifacts in the color-based channel images. In some embodiments, an opening filtering morphology operation is employed to remove the small artifacts in the images of the color-based channels. In some embodiments, the at least one image morphology filter includes filling small holes for the epithelial cell image data and the cell nuclei image data. In some embodiments, a closing image morphology operation is employed to fill the small holes for epithelial cell image data and the cell nuclei image data. In some embodiments, a watershed image morphology operation is employed to segment the lymphocyte image data to determine a location and an area for each lymphocyte within a tile. In some embodiments, the instructions executed on the one or more processors are further configured to: for each tile: 1) determine a total area of cell nuclei for the tile; 2) determine the total area of tumor region for the tile; 3) determine the total area of lymphocytes in the tumor region for the tile; 4) determine the total area of non-tumor region for the tile; 5) determine the total area of lymphocytes in the non-tumor region for the tile; 6) determine the total area of tumor margin for the tile; and 7) determine the total area of nuclei in the tumor margin for the tile; and one or more of: A) determine whether the tile is included in the aggregated tile results for patient level tumor infiltrating lymphocytes score based on whether the total area of cell nuclei for the tile meets a TILS minimum nuclei threshold and based on whether the total tumor region area meets a minimum tumor area threshold; B) determine whether the tile is included in the aggregated tile results for patient level non-tumor infiltrating lymphocytes score based on whether the total area of cell nuclei for the tile meets an NTILS minimum nuclei threshold and based on whether the total non-tumor region area meets a minimum non-tumor area threshold; and C) determine whether the tile is included in the aggregated tile results for patient level a non-tumor infiltrating lymphocytes at tumor margin score based on whether the total tumor margin area meets minimum tumor margin area threshold and based on the total area of cell nuclei in the tumor margin for the tile meets a minimum tumor margin nuclei threshold. In some embodiments, the patient level tumor infiltrating lymphocytes score is the median of the tile level tumor infiltrating lymphocytes scores for the tiles included in the aggregated tile level results for the tumor infiltrating lymphocytes score; the patient level non-tumor infiltrating lymphocytes score is the median of the tile level non-tumor infiltrating lymphocytes scores for the tiles included in the aggregated tile level results for the non-tumor infiltrating lymphocytes score; and the patient level non-tumor infiltrating lymphocytes at the tumor margin score is the median of the tile level non-tumor infiltrating lymphocytes at the tumor margin scores for the tiles included in the aggregated tile level results for the non-tumor infiltrating lymphocytes at the tumor margin score.

In some embodiments, a system also includes a scanner configured to digitalize at least one microscopy image of an IF pathology slide of the patient and store the resulting at least one digital microscopy image of the IF pathology slide of the patient in the one or more databases.

In some embodiments, the instructions executed on the one or more processors are further configured to transmit the classification of the patient to a user computing device with a computer display. In some embodiments, the computer display is configured to display the classification of the patient on the computer display.

In some embodiments, the instructions executed on the one or more processors are further configured to store the classification of the patient within the one or more databases.

In some embodiments, the system also includes parallel graphics processing units (GPUs) configured to perform GPU parallel image morphology operations.

In some embodiments, the system also includes an imaging system configured to obtain the immunofluorescence the at least one digital microscopy image of the immunofluorescence (IF) pathology slide of the patient.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1:
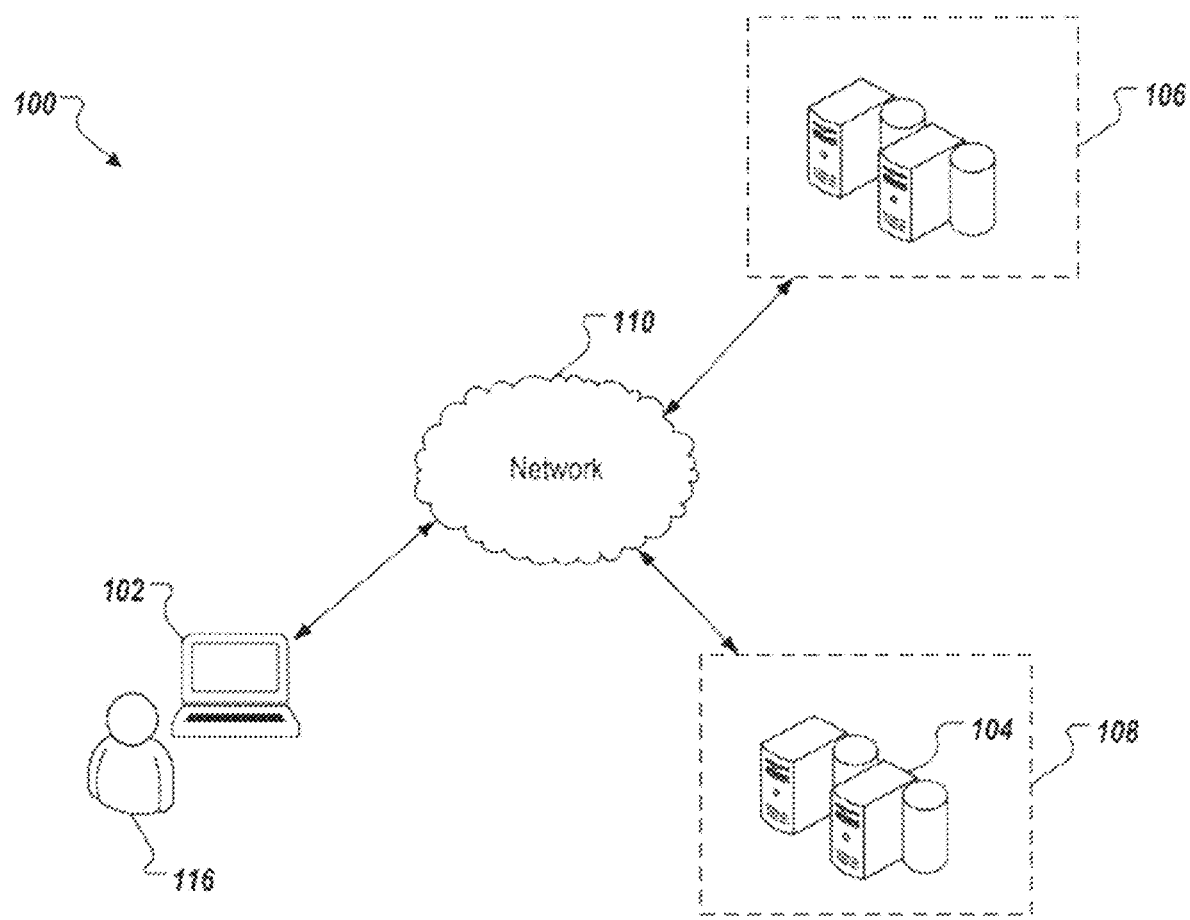
FIG. 1 schematically depicts an example environment that can be used to execute embodiments of the present disclosure.

Embodiments of the present disclosure include computer-implemented methods, systems, and non-transitory computer-readable storage media for automatically identifying tumor-immune phenotypes from digital immunofluorescence (IF) microscopy images of pathology slides of patients. The embodiments provide a quantitative measure and/or determination of a tumor-immune phenotype of a patient that is automatically determined based on analysis of a digital microscopy IF pathology image of the patient's tumor.

Traditionally, determining a patient's tumor-immune phenotype from the patient's pathology slides or slides was a subjective process based on the individual pathologist's analysis, resulting in discrepancies between pathologists and between analyses from the same pathologist but at different time. One approach to automated determination of a patient's tumor-immune phenotype employs a count ratio such as a count of cytotoxic lymphocytes divided by a count of tumor cells in a slide. However, a tumor cell count can be inaccurate due to overlapping tumor cells in a tumor nest. Further, pathologists often determine tumor-immune phenotypes by examining the density of immune cells. However, a count ratio may not accurately represent the density of immune cells in a sample because different types of tumor cells may have different sizes and thus the ratio of counts may not be consistent.

The described methods, systems, and non-transitory computer-readable media accurately provide a quantitative assessment of tumor-immune phenotype that is automatically determined using an image processing-based method that employs a density based tumor infiltrating lymphocytes score, a density based non-tumor infiltrating lymphocytes score, and a non-tumor infiltrating lymphocytes at tumor margin score. The tumor infiltrating lymphocytes score (TILS) measures the density of tumor infiltrating lymphocytes within the tumor cells. A higher TILS score indicates inflamed tumor cells. The non-tumor infiltrating lymphocytes score (NTILS) measures the density of tumor infiltrating lymphocytes outside of tumor cells, but inside the tumor environment, which may be described as between tumor cells. A higher NTILS score indicates that tumor cells are surrounded by tumor infiltrating lymphocytes and the phenotype is either inflamed or excluded, but not desert. The non-tumor infiltrating lymphocytes at tumor margin score (NTILS_margin), measures the density of tumor infiltrating lymphocytes outside of the tumor cells and inside the tumor margin. A higher NTILS_margin indicates that the tumor core is surrounded by tumor infiltrating lymphocytes and that the phenotype is either inflamed or excluded, but not desert.

In some embodiments, automated density based methods and systems for identifying tumor-immune phenotype described herein may reduce subjective error due to discrepancies between pathologists and more accurately identify tumor-immune phenotype than cell counting based methods.

In some embodiments, the described methods, systems, and non-transitory computer readable media are memory friendly and more efficient than models that employ deep learning as they do not require a complicated deep learning model to be stored in memory. Rather, the described methods, systems, and non-transitory computer readable media are based on memory friendly image morphology operations.

In some embodiments, the described methods, systems, and non-transitory computer readable media may employ parallel graphics processing units (GPUs). For example, the described methods, systems, and media may employ one or more GPUs in order to perform GPU parallel image morphology operations (e.g., at the image tile level). In some embodiments, this may enable the described methods, systems, and non-transitory computer readable media to perform multiple calculations across streams of data simultaneously for greater speed and efficiency.

FIG. 1 schematically depicts an example environment 100 that can be used to execute embodiments of the present disclosure. The environment 100 illustrates a user 116 that uses a computing device 102 to request identification of a tumor-immune phenotype based on an IF digital pathology slide. The computing device 102 is in communication with one or more databases 106, for example, through a network 110. In some embodiments, at least some or all of the one or more databases may be part of the computing device.

In some embodiments, the one or more databases 106 store at least one digital image of an IF pathology slide. In some embodiments, the one or more databases 106 store a training dataset of sample digital images of IF pathology slides. In some embodiments, the one or more databases 106 store a training dataset and a test dataset of IF pathology slides. In some embodiments, the one or more databases 106 provide the at least one digital image of an IF pathology slide and/or datasets to the computing device 102. In some embodiments, the computing device 102 uses the training datasets to determine thresholds for use with the patient level TILS, NTILS, and NTILS_margin scores to determine a tumor-immune phenotype from one or more IF digital pathology slides, as described in more detail below. In some embodiments, the computing device uses the testing datasets to evaluate the accuracy and sensitivity of the model in identifying a tumor-immune phenotype. In some embodiments, the thresholds for use with the patient level TILS, NTILS, and NTILS_margin scores were previously determined using the same or a different computer system. In some embodiments, the computing device 102 determines a tumor-immune phenotype of an IF pathology slide based on the predetermined thresholds. In some embodiments, alternatively, or in addition, the database 106 can provide the data to a computing device or computing system 108 that includes one or more processors 104 to perform the identification of a tumor-immune phenotype and the information regarding the tumor-immune phenotype can be provided by the computing device or computing system 108 to the user computing device 102. In some embodiments, a user 116 of the computing device 102 may provide the at least one digital image of an IF pathology slide for identification of a tumor-immune phenotype.

Figure 2:
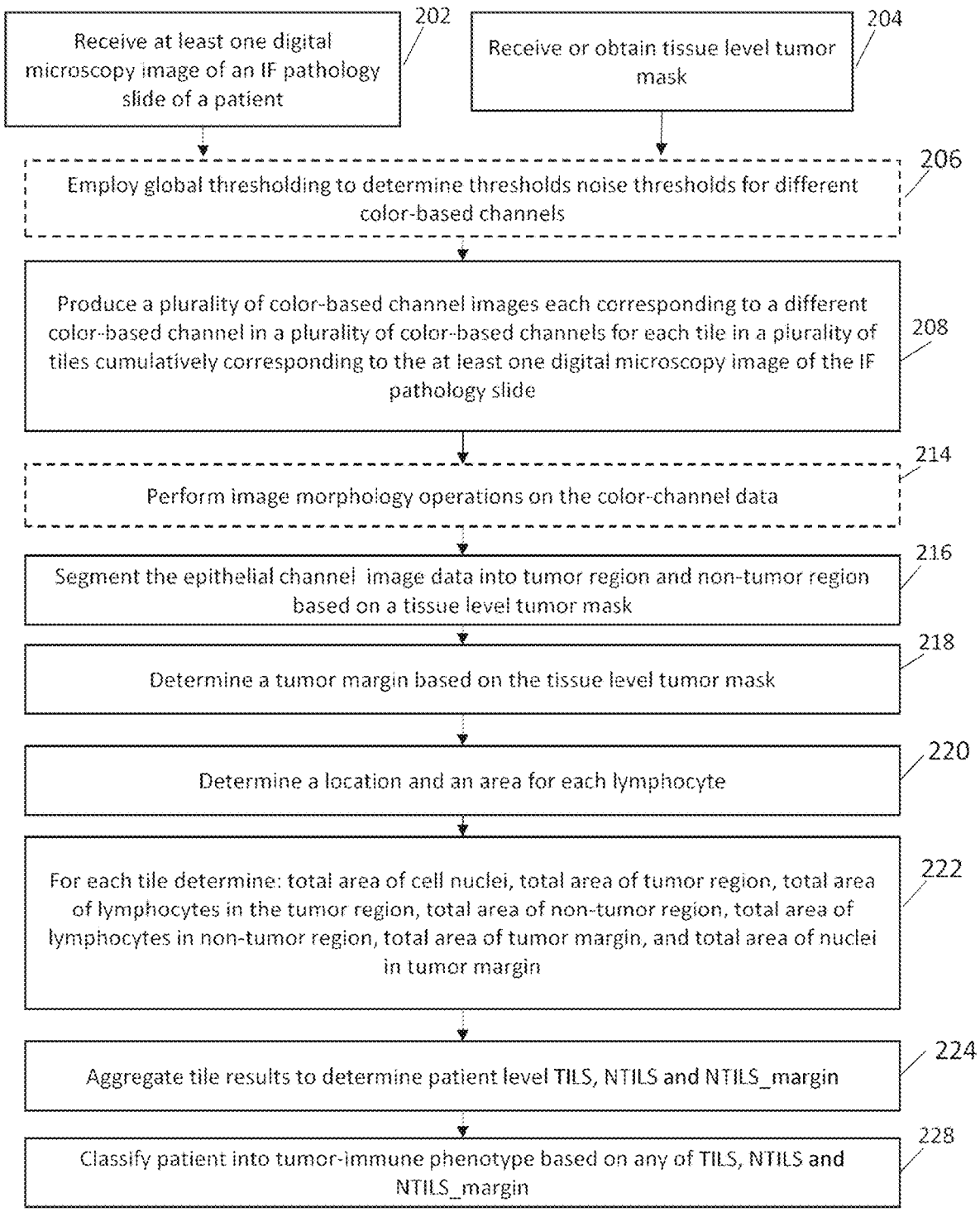
FIG. 2 is a flow chart of an example process that can be performed in accordance with some embodiments of the present disclosure.

FIG. 2 depicts an example method 200 that can be executed in accordance with some embodiments of the present disclosure to determine an identification of a tumor-immune phenotype based on one or more IF pathology slides. One or more steps of the method can be executed by one or more computing devices or computing systems (e.g., the computing devices 102 or 108 in FIG. 1).

Immunofluorescence Pathology Images and Immunofluorescence Staining

The method schematically depicted in FIG. 2 includes receiving (e.g., from one or more databases) at least one digital microscopy image of an immunofluorescence (IF) pathology slide of a patient (202 of FIG. 2). In some embodiments, the at least one digital microscopy image of an IF pathology slide is obtained or received from a user or from some other source.

Producing immunofluorescence pathology slide images requires immunofluorescence staining, which is an antigen-detection test that is used primarily on tissue sections, cell smears, or cultured cells. In some embodiments described herein, the staining should include stains that identify epithelial cells (e.g., pan cytokeratin (pan-CK)), cell nuclei (e.g., 4',6-diamidino-2-phenylindole (DAPI)), and cytotoxic lymphocytes (e.g., CD8+ T cells, CD3+T, and/or natural killer (NK) cells). In an example described below, stains are used to stain three channels for analysis in the resulting immunofluorescence images: epithelial cells using pan-CK, cell nuclei using DAPI, and CD8+ lymphocytes, with an additional stain for CD3+ lymphocytes used merely to check results. However, it will be understood that more or fewer stains and/or more or fewer channels may be employed without departing from the spirit and scope of the present disclosure.

In an exemplary embodiment, a pan-CK stain is used to stain epithelial cells. In the immunofluorescence (IF) pathology slide images most of the epithelial cells are tumor cells because they are taken from tumor biopsy samples. In the exemplary embodiment, after immunofluorescence staining is performed, the pan-CK-stained epithelial cells appear with orange fluorescence.

In an exemplary embodiment, a DAPI stain is utilized to stain cell nuclei. In the exemplary embodiment, after immunofluorescence staining is performed, the cell nuclei appear with blue fluorescence. Occasionally, artifacts may also be stained during this process.

In an exemplary embodiment, a stain that specifically stains the CD8+ lymphocytes is employed. In some embodiments, a stain that specifically stains CD3+ lymphocytes may also be employed. In some embodiments, IF staining is used to stain the CD8+ and/or CD3+ lymphocytes. In some embodiments, the IF staining uses CD3+antibody Clone F7.2.38 and/or CD8 clone antibody SP16.

In the exemplary embodiment, after immunofluorescence staining is performed, the CD8+ lymphocytes appear with green fluorescence and the CD3+ lymphocytes appear with red fluorescence. Occasionally, red blood cells may also catch these stains. In some embodiments, the cell nuclei channel is used to exclude false CD3 and CD8 staining of red blood cells.

After staining, microscopy images of the IF pathology slide(s) are digitalized (for example, using a slide image scanner) and stored as stained tissue image(s) in a database (e.g., the database 106 in FIG. 1) communicatively coupled to the computing device. In some embodiments, the microscopy images may be initially captured in digital form.

The method also includes receiving or obtaining a tissue level tumor mask identifying which portion or portions of the digital microscopy image correspond to one or more tumor nests (204 of FIG. 2). The tissue level tumor mask is based on pathologist annotation in some embodiments. In some embodiments, the annotation is performed by a pathologist using a hematoxylin-eosin (H&E) stained image. In some embodiments, the annotation is performed by a pathologist using the IF pathology slide image.

Image Preprocessing

Figure 3:
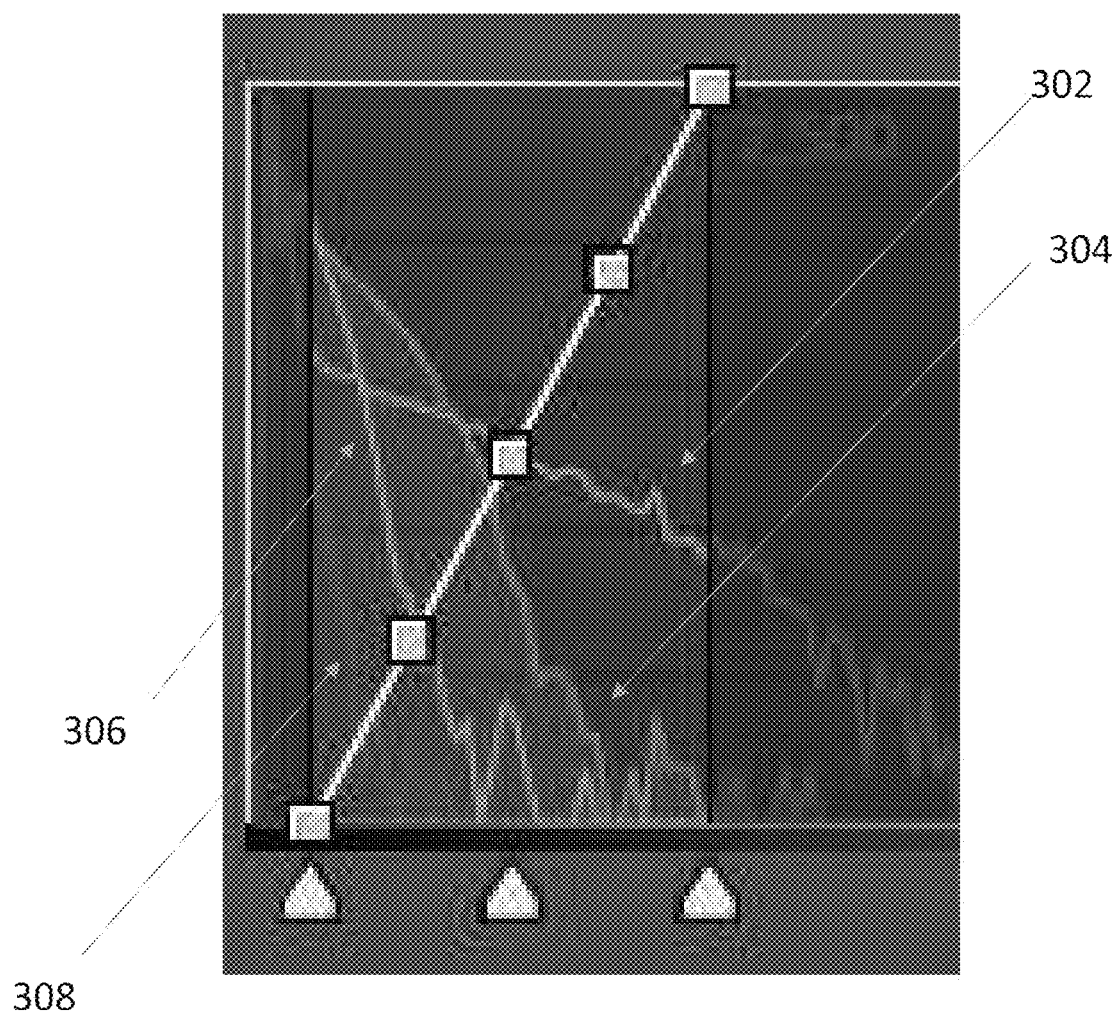
FIG. 3 schematically depicts global thresholding for noise reduction in immunofluorescence images in accordance with some embodiments of the present disclosure.

In some embodiments, the at least one digital microscopy image of an IF pathology slide of a patient is preprocessed prior to being divided into tiles. For example, in some embodiments, global thresholding is used for noise reduction in immunofluorescence images by separating signal from background noise (206 of FIG. 2). In some embodiments, the global thresholding is conducted separately for each color-based channel image corresponding to data from different types of markers. In some embodiments, a color deconvolution of the whole at least one digital microscopy image is performed to obtain a different color-based channel image for each different color-based channel before determining the global thresholding. The color-based channel global thresholding is illustrated in FIG. 3 in which 302 corresponds to a pixel intensity histogram from epithelial cell markers (orange line), pixel intensity histogram from cell nuclei markers corresponds to 304 (blue line), pixel intensity histogram from CD8+ lymphocyte markers corresponds to 306 (green line), and pixel intensity histogram from CD3+ lymphocyte markers corresponds to 308 (red line). A pixel intensity histogram is a graph of pixel intensity (on the x-axis) versus number of pixels (on the y-axis). The global thresholding identifies pixels above or below a particular threshold value. Pixels at or above the threshold value are classified as signals and pixels below the threshold value are classified as background noise. The global thresholding is channel-specific for channels corresponding to signal from different types of markers and is adaptive for each whole slide image. For each tile in each channel (e.g., epithelial cells 502, nuclei cells 504, CD8+ positive lymphocytes 506, and CD3+ positive lymphocytes 508 of FIG. 5), the computing device employs the median and standard deviation based thresholding to separate the signal from the noise, where the median and standard deviation is evaluated for each color-channel whole slide image, respectively. As used herein, the terms "whole slide image" and "full image" are used to differentiate a full untiled image (e.g., the at least one digital microscopy image or a deconvolved color-based channel image of the at least one digital microscopy image) from an individual image tile that is one of a plurality of image tiles that collectively form a full image. In one embodiment, the following threshold calculation is used for global thresholding of the epithelial cell channel:

Threshold value$_{color\text{-}based\ channel}$=(median of positive pixel value within tissue level tumor mask)$_{color\text{-}based\ channel\ full\ image}$+1.5×(standard deviation of positive pixel value within tissue level tumor mask)$_{color\text{-}based\ channel\ full\ image}$.

Adaptively for each whole slide image, each channel has its own global threshold that applies to all channel images associated with that channel. In some embodiments, the computing device may employ other thresholding methods, for example, but not limited to, Otsu's thresholding, fixed thresholding, and median and variance based thresholding.

In FIG. 2, step 206 is indicated with broken lines as this step may not be performed in some embodiments. For example, in some embodiments the received at least one digital microscopy image of an IF pathology slide of a patient may already have been preprocessed to separate signal from background noise. In some embodiments, channel-specific thresholds may be provided with the at least one digital microscopy image of an IF pathology slide of a patient.

Tiling

A plurality of color-based channel images is produced each color-based channel image corresponding to a different color-based channel in a plurality of color-based channels for each image tile in a plurality of image tiles cumulatively corresponding to the at least one digital microscopy image of the IF pathology slide (208 of FIG. 2).

In some embodiments the computing device divides the at least one digital microscopy image of the IF pathology slide into a plurality of image tiles, and creates the plurality of color-based channel images for each of the plurality of image tiles from the corresponding image tile using color deconvolution as described below.

In other embodiments, the computing device creates a plurality of full image, color-based, channel images from the at least one digital microscopy image using color deconvolution, and then divides each of the plurality of full image, color-based channel images into tiles to form the plurality of color-based channel images for each of the plurality of image tiles.

Figure 4:
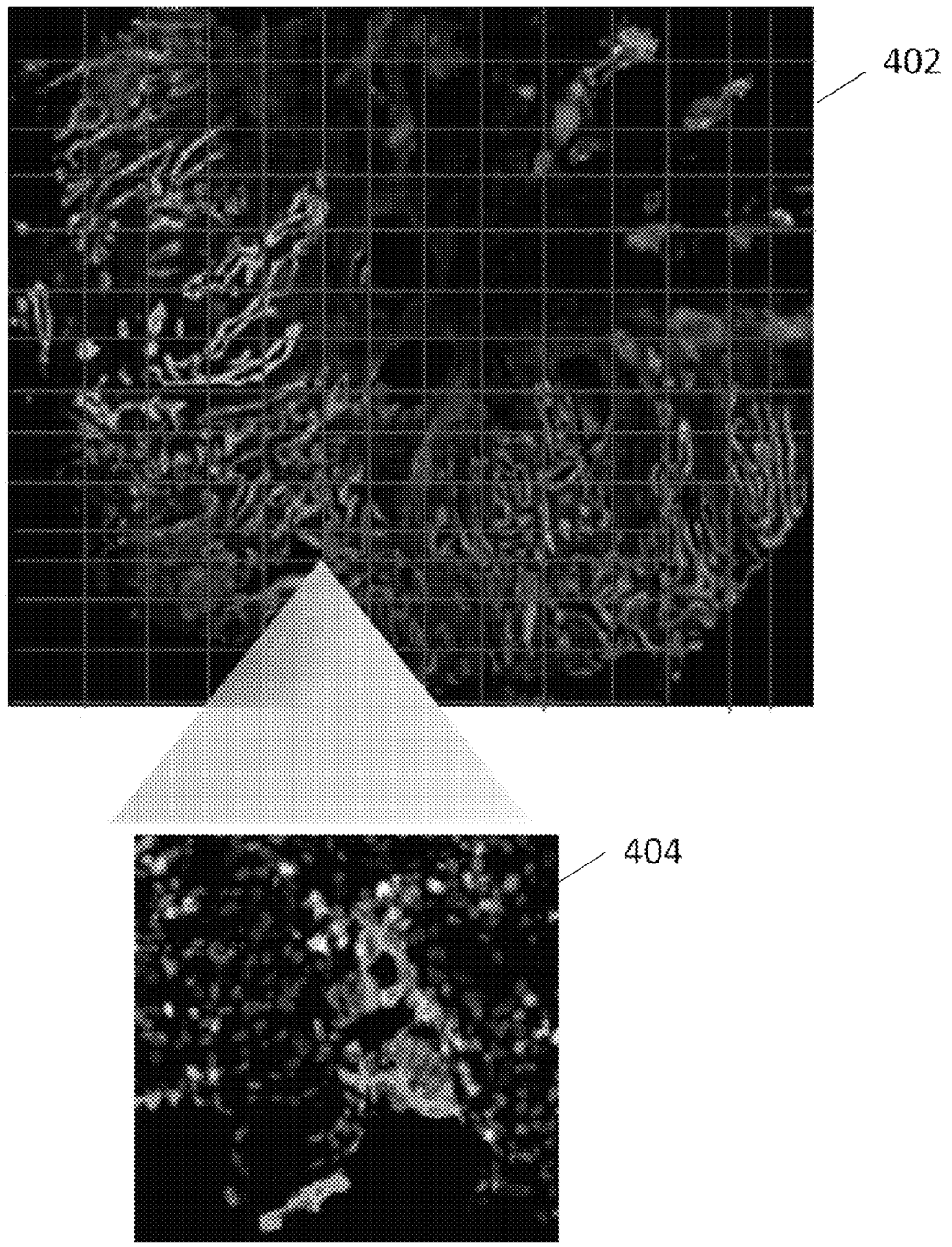
FIG. 4 schematically depicts a segmentation of a digital microscopy image of an IF pathology slide image into tiles in accordance with some embodiments of the present disclosure.

As illustrated in FIG. 4, in one embodiment, the computing device divides the digital microscopy image 402 of the IF pathology slide into image tiles 404. In some embodiments, a size of a tile is large enough to cover about a hundred tumor cells, but smaller than the size of a pre-specified tumor margin. In an exemplary embodiment, a size of a tile is 2500 pixels by 2500 pixels corresponding to 125 microns by 125 microns of the sample.

The pixel size of each tile may also depend on the magnification of the digital image. For example, for 20× magnification, a tile size within the range of 500 to 5000 pixels per side may be employed in some embodiments as long as the tile covers a sufficient amount of tumor cells.

Color Deconvolution

Figure 5:
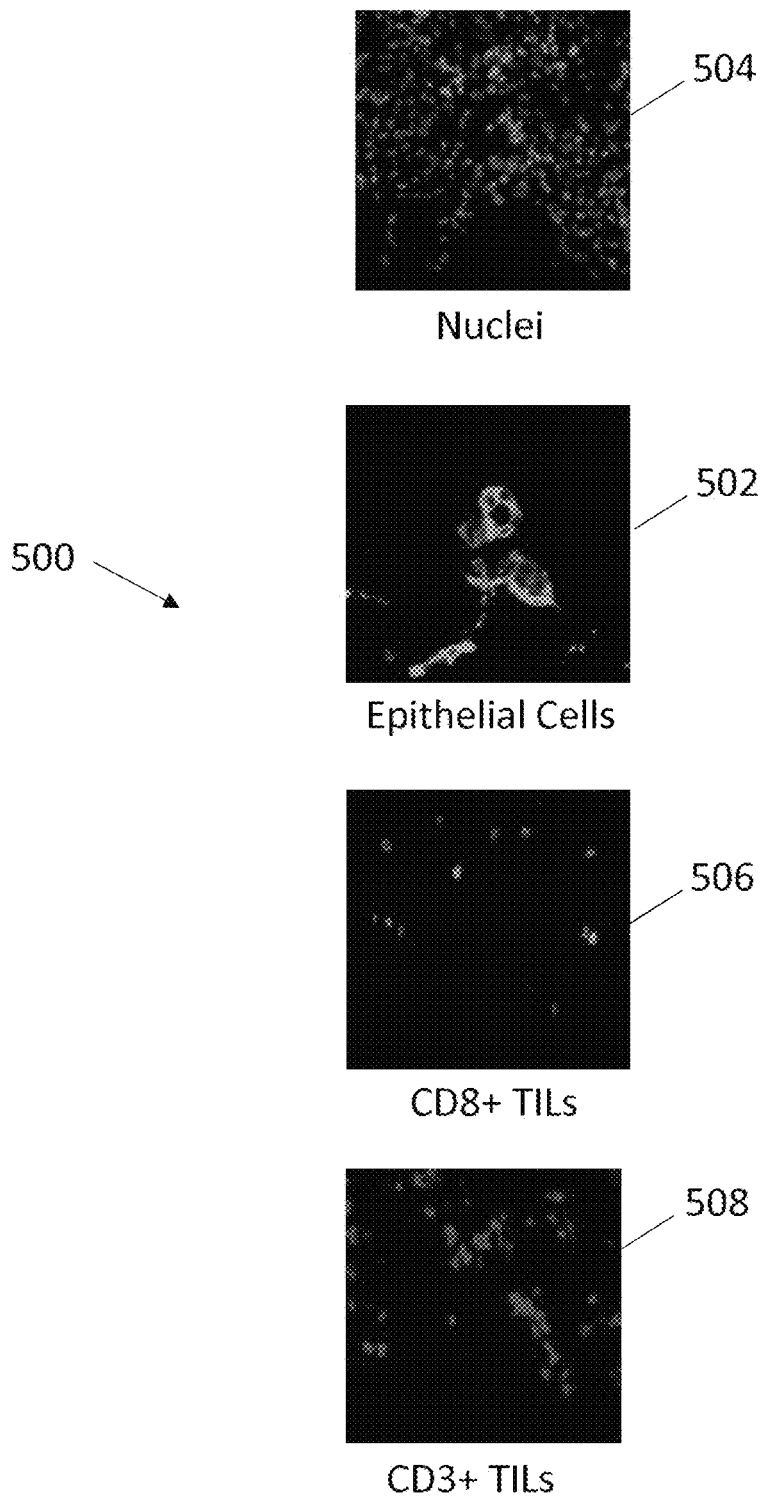
FIG. 5 includes images illustrating performing color deconvolution on a tile of the digital image to create biologically meaningful channel images in accordance with some embodiments of the present disclosure.

As illustrated in FIG. 5, in some embodiments, the computing device employs color deconvolution 500 on each image tile of the digital image to create biologically meaningful channels each corresponding to a different stain for the image tile. Each channel of the image corresponds to a different stain. In an exemplary embodiment, the computing device uses color deconvolution to separate the stained tissues and cells in the digital image into channels, corresponding to the colors of the stains used. The computing device creates a plurality of color-based channel images each corresponding to a color-based channel in a plurality of color-based channels for each of the plurality of tiles using color deconvolution. In some embodiments, the plurality of color-based channels includes an epithelial cell channel including epithelial cell image data, a cell nuclei channel including cell nuclei image data, and at least one lymphocyte channel including lymphocyte image data.

In an exemplary embodiment, there are at least three channels corresponding to epithelial cells 502, cell nuclei 504, and cytotoxic lymphocytes (e.g., CD8+ lymphocytes) 506. In some embodiments, there is also a fourth channel corresponding to another type of cytotoxic lymphocytes (e.g., CD3+ lymphocytes) 508. In other embodiments, more or fewer channels may be employed. For example, in some embodiments, three channels are used, epithelial cells, nuclei cells, and CD8+ lymphocytes. It will be understood that more or fewer channels may be used without departing from the spirit and scope of the present disclosure. Additionally, in some of the tiles, one or more of these channels may be missing (for example, there may be no lymphocytes present).

In some embodiments, channels corresponding to other types of cytotoxic lymphocytes may be employed, such as NK (natural killer) cells. In some embodiments, at least one lymphocyte channel includes cytotoxic lymphocyte image data. In some embodiments, at least one lymphocyte channel includes CD8+ T cell image data. In some embodiments, at least one lymphocyte channel includes CD3+ T cell image data. In some embodiments, at least one lymphocyte channel includes natural killer (NK) cytotoxic lymphocyte image data. In some embodiments, the at least one lymphocyte channel includes multiple lymphocyte channels including any of CD8+ T cell image data, CD3+ T cell image data, and natural killer (NK) cytotoxic lymphocyte image data.

In some embodiments, an epithelial cell channel includes pan cytokeratin (pan-CK) stained image data. In some embodiments, a cell nuclei channel includes 4',6-diamidino-2-phenylindole (DAPI) stained image data.

In some embodiments, the channel-based global thresholds determined from each digital microscopy image and the tissue level tumor masks (206 of FIG. 2) are applied to all image tiles in the corresponding color-channel.

In some embodiments, image morphology operations may be performed on the color-channel image data (214 of FIG. 2). This step is indicated with broken lines as image morphology operations may not be employed in all embodiments. Example image morphology operations that may be performed are described below.

Correct Out-of-Focus Regions and Staining Artifacts for all Channels

Figure 6:
FIG. 6 is a nuclei channel image containing out-of-focus regions to be corrected and staining artifacts to be removed in accordance with some embodiments of the present disclosure.

As illustrated in FIG. 6, in some embodiments, the computing device corrects out-of-focus regions and removes staining artifacts for all channels. In an exemplary embodiment, the computing device employs top-hat filtering, which is an image morphology operation used by the computing device for baseline removal to correct out-of-focus region and staining artifacts. In some embodiments, the computing device performs top-hat filtering on each channel image to return an image containing objects or elements of the input image that are smaller than a predefined size of a kernel for removal.

The size, or width, of elements that are extracted by top-hat filtering can be controlled by the choice of the kernel. In an exemplary embodiment, a kernel is chosen that is larger than a size of the largest cells but smaller than the smallest artifact or region out-of-focus, such that the filtering removed the artifacts but not the cells. In a non-limiting example, a kernel size of 75 pixels is used, where 75 pixels correspond to about 3.75 microns.

Figure 7:
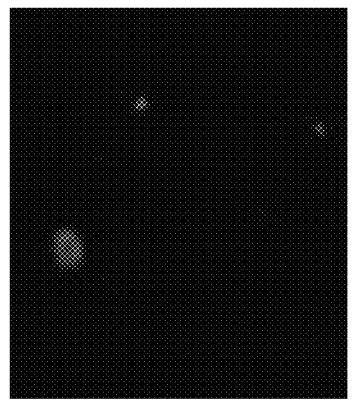
FIG. 7 is a lymphocyte channel image including small artifacts to be removed in accordance with some embodiments of the present disclosure.

As illustrated in FIG. 7, in some embodiments, the computing device removes small artifacts for each channel image for all channels. In some embodiments, the computing device uses Opening, which is an image morphology operation that removes small objects from the foreground of an image. In an exemplary embodiment, a kernel is chosen that is larger than the largest size of the small artifacts but smaller than the smallest cells, such that the filtering removes the artifacts but not the cells. In some embodiments, different kernels may be employed for at least some of the channels. In a non-limiting example, a kernel size of 20 pixels (corresponding to about 1 micron) is used for the epithelial channel while a kernel size of 5 pixels (corresponding to about 0.25 micron) is used for the remaining channels.

Fill Small Holes for Epithelial Cell Channel and Nuclei Channel

Figure 8:
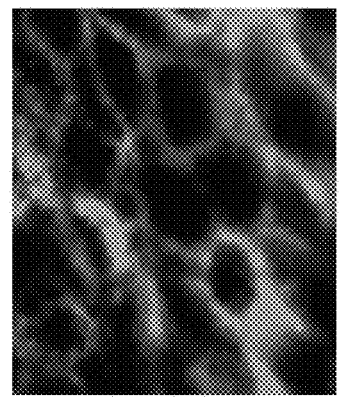
FIG. 8 is an epithelial cell channel image containing small holes to be filled in accordance with some embodiments of the present disclosure.

As illustrated in FIG. 8, in some embodiments, the computing device fills small holes for the epithelial cell channel and the cell nuclei channel. In some embodiments, the computing device employs Closing, which is an image morphology operation that closes small holes in the foreground of an image based on a predefined kernel size. In a non-limiting example, a kernel size of 35 pixels (about 1.75 microns) is used for the epithelial channel, while a kernel size of 10 pixels (about 0.5 microns) is used for the cell nuclei channel.

Figure 9:
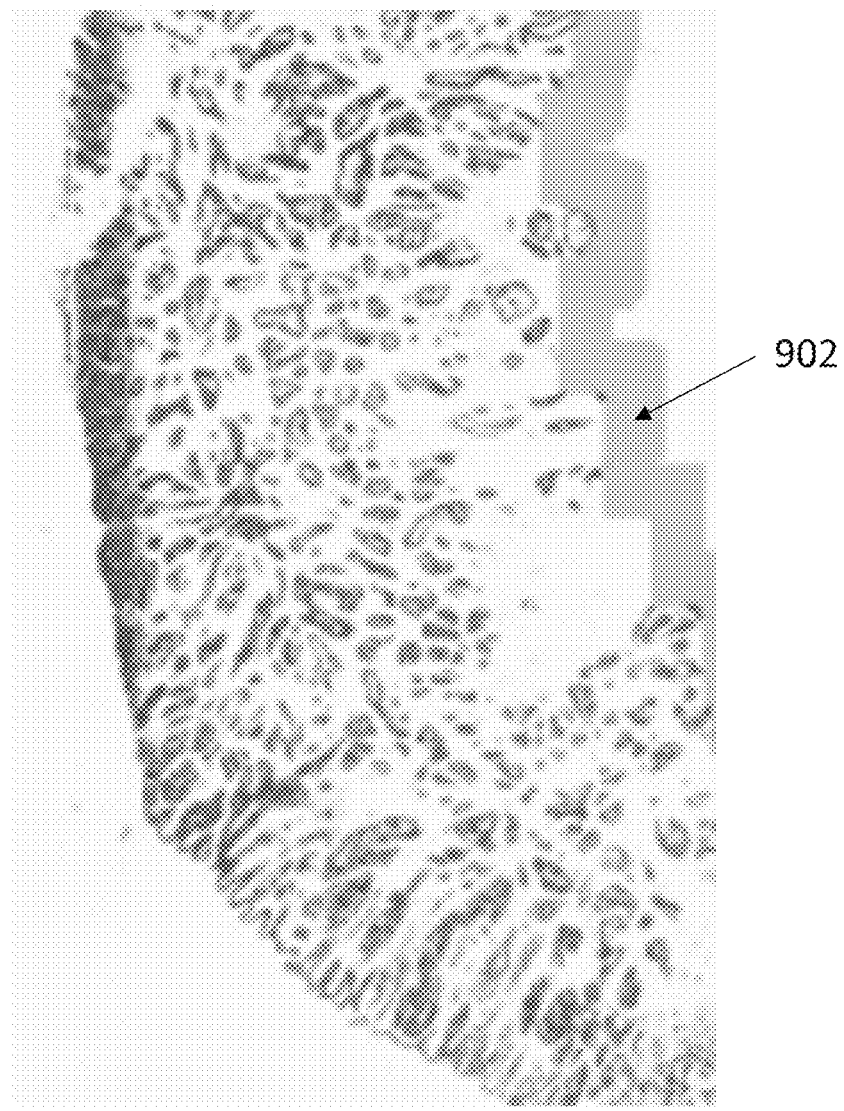
FIG. 9 is a tissue level image indicating a tumor area and non-tumor area in accordance with some embodiments of the present disclosure.

Identification and Localization of Tumor and Non-Tumor Regions, Tumor Margin, and Lymphocytes For at least some of the tiles, the computing device segments the epithelial channel image for the tile into a tumor region and a non-tumor region based on a tissue level tumor mask (216 of FIG. 2). Tumor localization may be evaluated using automatically and/or manually obtained segmentation masks, for example, using computer-generated segmentation masks and/or manually hand-drawn segmentation masks from a pathologist. For example, the computing device receives or obtains a tissue level tumor mask based on pathologist annotation identifying which portion or portions of the digital microscopy image correspond to one or more tumor nests. In another example, the computing device performs this segmentation using the tissue level tumor mask and the epithelial channel data. As illustrated in FIG. 9, in one embodiment, the identified tumor region 902 appears orange (referenced as the tumor area) and the identified non-tumor region appears white 904 (referenced as the non-tumor area).

For at least some of the image tiles, the computing device determines a tumor margin region that is mapped onto the image tile based on a pre-specified margin outside a boundary of the tumor region based on the tissue level tumor mask (218 of FIG. 2). In some embodiments, the pre-specified tumor margin is determined from the full microscopy image at the tissue level and then mapped onto the tiles. In some embodiments, the pre-specified margin falls within a range of 500 microns (μm) to 1000 microns, which may translate to about 1000 to 2000 pixels for images or tiles with 20 pixels per micron. In some embodiments, the pre-specified tumor margin is cancer-type specific. FIG. 9 is a tissue level image with orange indicating the epithelial cells and gray indicating the tumor margin 902. The tumor margin is the region outside of the boundary of the tissue level tumor mask by a pre-specified margin and is located between healthy tissue and the tumor nest.

Figure 10:
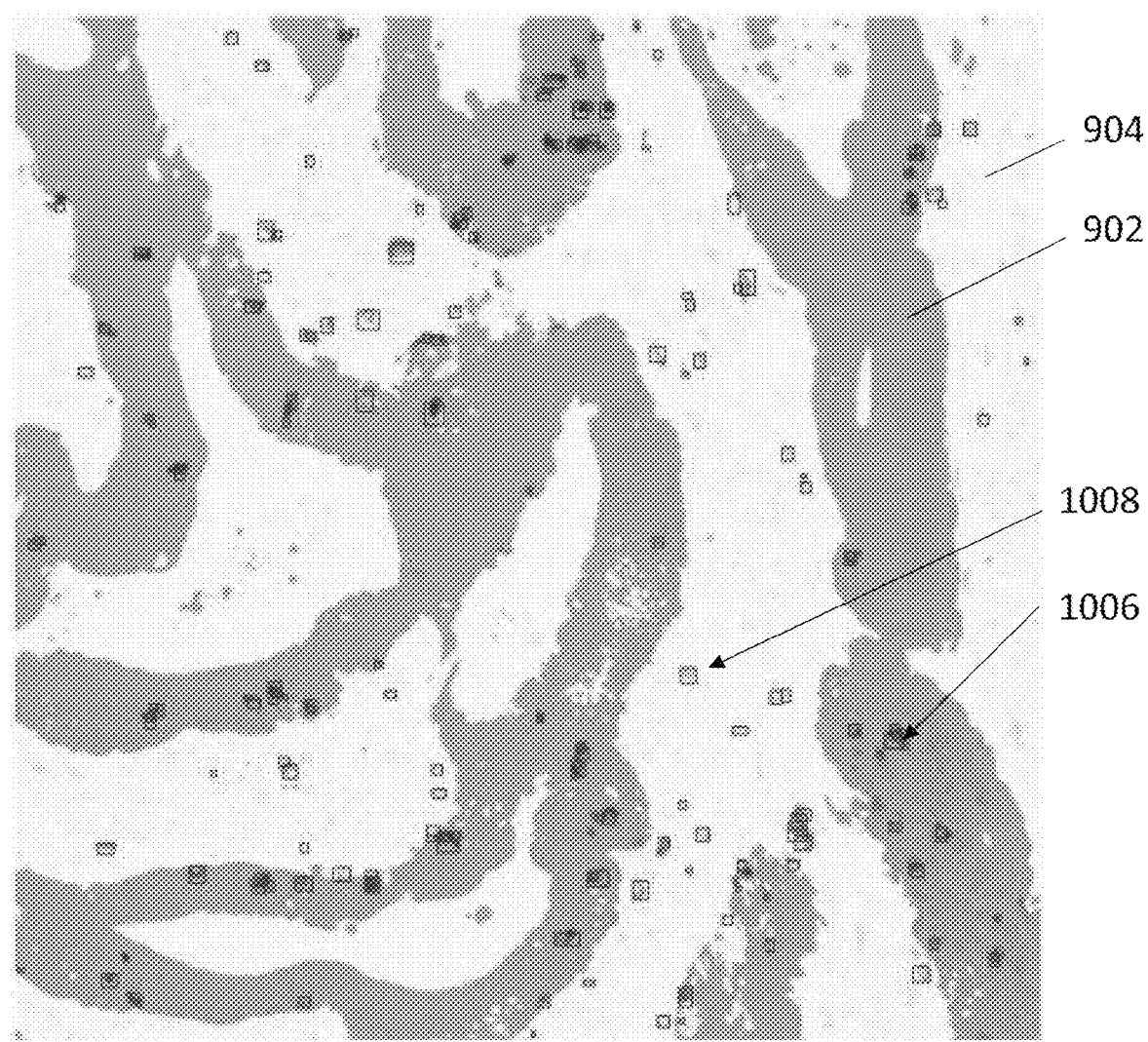
FIG. 10 is an image of a tumor and a non-tumor region mask applied to the lymphocyte channel including segmentation of the tumor and non-tumor regions and segmentation of lymphocytes in accordance with some embodiments of the present disclosure.

For the tiles including lymphocyte image data, the computing device may determine a location and an area for each lymphocyte (e.g., CD8+ lymphocyte) within the tile (220 of FIG. 2). The determination of a location and an area for each lymphocyte may employ segmentation in some embodiments. In some embodiments, a watershed image morphology operation may be employed to segment the lymphocytes. Watershed is an algorithm used for segmentation, that is, for separating different objects in an image. In some embodiments, once segmentation is performed, the computing device generates a bounding box for each segmented lymphocyte (e.g., CD8+ lymphocyte) to locate each lymphocyte (e.g., CD8+ lymphocyte) and identify whether the lymphocyte is located within the tumor region or within the non-tumor region. The area of each lymphocyte is determined based on the staining of the lymphocyte within the boundary as determined by Watershed segmentation in some embodiments. As illustrated in FIG. 10, which displays the tumor and non-tumor region mask applied to the lymphocyte channel, in some embodiments, the computing device generates a red bounding box 1006 for each lymphocyte (e.g., CD8+ lymphocyte) located within the tumor region, which is indicated in tan, and generates a green bounding box 1008 for each lymphocyte (e.g., CD8+ lymphocyte) located within the non-tumor region, which is indicated in cream.

In some embodiments, the processed channel data, tumor and non-tumor region data, tumor margin data and lymphocyte localization data is used to determine measurements for each of at least some of the tiles or all of the tiles in the plurality, the measurements for the tile including: a total area of cell nuclei in the tile, a total area of the tile that is tumor region, a total area of the tile that is tumor margin (set to zero if there is no tumor margin), a total area of the lymphocytes in the tumor region, a total area of the tile that is non-tumor region, a total area of the lymphocytes in the non-tumor region of the tile, and a total area of the tile that is tumor margin (222 of FIG. 2).

Calculation of TILS, NTILS or/and NTILS_Margin and Aggregation of Tile Level Results The computing device aggregates results from tiles to determine a patient level tumor infiltrating lymphocytes score (TILS), a patient level non-tumor infiltrating lymphocytes score (NTILS), or/and a patient level non-tumor infiltrating lymphocytes at tumor margin score (NTILS_margin) (224 in FIG. 2). The TILS measures the density of tumor infiltrating lymphocytes inside the tumor microenvironment. A higher TILS indicates inflamed tumor cells. The NTILS measures the density of tumor infiltrating lymphocytes outside of tumor cells. A higher NTILS indicates tumor cells are surrounded by tumor infiltrating lymphocytes and the phenotype is either inflamed or excluded, but not desert. The NTILS_margin measures the density of tumor infiltrating lymphocytes outside of tumor cells and inside the tumor margin. A higher NTILS_margin indicates that the tumor core or tumor nest is surrounded by tumor infiltrating lymphocytes and the phenotype is either inflamed or excluded but not desert.

In some embodiments, the patient level scores are based on tile level scores. For example, in some embodiments, the computing device calculates the TILS, the NTILS, and the NTILS_margin at the tile level.

For at least some of the tiles, the computing device calculates a tumor infiltrating lymphocytes score (TILS) based on a total area of the lymphocytes in the tumor region of the tile and a total area of the tumor region for the tile. In some embodiments, the tumor infiltrating lymphocytes score (TILS) for a tile is determined based on the total area of the lymphocytes in the tumor region for the tile divided by the total area of the tumor region for the tile.

For at least some of the tiles, the computing device calculates a non-tumor infiltrating lymphocytes score (NTILS) based on a total area of the lymphocytes in the non-tumor region of the tile excluding lymphocyte area in the tumor margin area if there is any and a total area of the non-tumor region of the tile excluding tumor margin area if there are any. In some embodiments, the non-tumor infiltrating lymphocytes score (NTILS) for a tile is determined based on the total area of the lymphocytes in the of the non-tumor region of the tile divided by total area of the non-tumor region of the tile.

For at least some of the tiles, the computing device calculates a non-tumor infiltrating lymphocytes at tumor margin score (NTILS_margin) based on a total area of lymphocytes in the tumor margin and a total area of the tumor margin for the tile. In some embodiments, the non-tumor infiltrating lymphocytes at tumor margin score (NTILS_margin) is determined based on the on a total area of lymphocytes in the tumor margin divided by the total area of the tumor margin for the tile.

In some embodiments, the TILS, the NTILS and the NTILS_margin at the tile level are calculated based on the following equations:

$$TILS_{tile} = \frac{\text{lymphocyte area in tumor region}}{\text{area of tumor region}}$$

$$NTILS_{tile} = \frac{\text{lymphocyte area in non-tumor region}}{\text{area of non-tumor region excluding area in tumor margin if any}}$$

$$NTILS\_margin_{tile} = \frac{\text{lymphocyte area in tumor margin}}{\text{area of tumor margin}}$$

In some embodiments, filtering is applied to determine which tiles will be aggregated for the patient level TILS. For example, in some embodiments, a tile is only used for aggregation for the patient level TILS if the tile meets the inclusion criterion of (1) sufficient cell nuclei (e.g., greater than a pre-specified threshold percentage of the tile area is cell nuclei), and (2) sufficient tumor region (e.g., greater than a pre-specified threshold percentage of the tile area is tumor region). In some embodiments, the pre-specified threshold for percentage of the area of the tile being cell nuclei for a tile to be included in patient level TILS is 1%. In some embodiments, the pre-specified threshold for percentage of the area of the tile being cell nuclei for a tile to be included in patient level TILS may be in a range of 0.1% to 10%. In some embodiments, the pre-specified threshold for percentage of the area of the tile being tumor region for a tile to be included in patient level TILS is 10%. In some embodiments, the pre-specified threshold for percentage of the area of the tile being tumor region for a tile to be included in patient level TILS falls in a range of 1% to 20%.

In some embodiments, filtering is applied to determine which tiles will be aggregated for the patient level NTILS. For example, in some embodiments, a tile is only used for aggregation for the patient level NTILS if the tile meets the inclusion criterion of (1) sufficient cell nuclei (e.g., greater than a pre-specified threshold percentage of the tile area is cell nuclei), and (2) sufficient non-tumor region (e.g., greater than a pre-specified threshold percentage of the tile area is non-tumor region). In some embodiments, the pre-specified threshold for percentage of the area of the tile being cell nuclei for a tile to be included in patient level NTILS is 1%. In some embodiments, the pre-specified threshold for percentage of the area of the tile being cell nuclei for a tile to be included in patient level NTILS may be in a range of 0.1% to 10%. In some embodiments, the pre-specified threshold for percentage of the area of the tile being non-tumor region for a tile to be included in patient level NTILS is 1%. In some embodiments, the pre-specified threshold for percentage of the area of the tile being non-tumor region for a tile to be included in patient level NTILS falls in a range of 0.1% to 10%.

In some embodiments, filtering is applied to determine which tiles will be aggregated for the patient level NTILS_margin. For example, in some embodiments, a tile is only used for aggregation for the patient level NTILS_margin if the tile meets the inclusion criterion of (1) sufficient tumor margin area (e.g., greater than a pre-specified threshold percentage of the tile area is tumor margin), and (2) sufficient nuclei in the tumor margin (e.g., greater than a pre-specified threshold percentage of the tile area in the tumor margin that is cell nuclei). For example, only the tiles that contain a sufficient amount of tumor margin is included in the aggregation. In some embodiments, the area of the nuclei in the tumor margin is set to zero if the tile does not contain any tumor margin.

In some embodiments, the pre-specified threshold for percentage of the area of the tile being tumor margin for a tile to be included in patient level NTILS_margin is 40%. In some embodiments, the pre-specified threshold for percentage of the area of the tile being tumor margin for a tile to be included in patient level NTILS_margin falls in a range of 10% to 100%. In some embodiments, the pre-specified threshold for percentage of the area of the tile being cell nuclei in the tumor margin for a tile to be included in patient level NTILS_margin is 0.1%. In some embodiments, the pre-specified threshold for percentage of the area of the tile being cell nuclei in the tumor margin for a tile to be included in patient level NTILS_margin may be in a range of 0.01% to 5%.

Patient level TILS, NTILS, and NTILS_margin scores are determined based on tiles that are included in the respective aggregation. In some embodiments, this may be described as the patient level NTILS, NTILS, and NTILS_margin being functions of the tile level statistics for tiles included in the respective aggregation.

$$TILS_{patient} = f_{TILS}(\text{title level statistics}_{aggregated\ tiles_{TILS}})$$

$$NTILS_{patient} = f_{NTILS}(\text{title level statistics}_{aggregated\ tiles_{NTILS}})$$

$$NTILS\_margin_{patient} = f_{NTILS\_margin}(\text{title level statistics}_{aggregated\ tiles_{NTILS\_margin}})$$

In some embodiments, the patient level TILS is the median of the tile level TILS for tiles that were aggregated for the patient level TILS. In some embodiments, the patient level NTILS is the median of the tile level NTILS for tiles that were aggregated for the patient level NTILS. In some embodiments, the patient level NTILS_margin is the median of the tile level NTILS_margin for tiles that were aggregated for the patient level NTILS_margin. This may be expressed in terms of the functions above as follows:

$$TILS_{patient} = f_{TILS} = \text{median}^*\{TILS_{tile}\}_{aggregated\ tiles_{TILS}}$$

$$NTILS_{patient} = f_{NTILS} = \text{median}(\{NTILS_{tile}\}_{aggregated\ tiles_{NTILS}})$$

$$NTILS\_margin_{patient} = f_{TILS\_margin} = \text{median}(\{NTILS\_margin_{tile}\}_{aggregated\ tiles_{NTILS\_margin}})$$

In some embodiments, the patient level TILS is the mean of the tile level TILS for tiles that were aggregated for the patient level TILS. In some embodiments, the patient level NTILS is the mean of the tile level NTILS for tiles that were aggregated for the patient level NTILS. In some embodiments, the patient level NTILS_margin is the mean of the tile level NTILS_margin for tiles that were aggregated for the patient level NTILS_margin. This may be expressed in terms of the functions above as follows:

$$TILS_{patient} = f_{TILS} = \text{mean}(\{TILS_{tile}\}_{aggregated\ tiles_{TILS}})$$

$$NTILS_{patient} = f_{NTILS} = \text{mean}(\{NTILS_{tile}\}_{aggregated\ tiles_{NTILS}})$$

$$NTILS\_margin_{patient} = f_{TILS\_margin} = \text{mean}(\{NTILS\_margin_{tile}\}_{aggregated\ tiles_{NTILS\_margin}})$$

In some embodiments, tile level TILS, NTILS, and NTILS_margin may not be calculated, but instead tiles whose tile level statistics are aggregated for patient level score are used to determine a patient level score based on cumulative values for all the aggregated tiles. For example, in some such embodiments, patient level TILS, NTILS and NTILS_margin may be calculated according to the following equations:

$$TILS_{patient} = f_{TILS} = \frac{\sum_{aggregated\ tiles_{TILS}} (\text{lymphocyte area in tumor region})}{\sum_{aggregated\ tiles_{TILS}} (\text{area of tumor region})}$$

$$NTILS_{patient} =$$

$$f_{NTILS} = \frac{\sum_{aggregated\ tiles_{NTILS}} (\text{lymphocyte area in non-tumor region excluding } lyphocyte \text{ area in tumor margin})}{\sum_{aggregated\ tiles_{NTILS}} (\text{area of non-tumor region})}$$

$$NTILS\_margin_{patient} = f_{TILS\_margin} =$$

$$\frac{\sum_{aggregated\ tiles_{NTILS\_margin}} (\text{lymphocyte area in tumor margin})}{\sum_{aggregated\ tiles_{NTILS\_margin}} (\text{area of tumor margin})}$$

Patient Level Classification

Figure 11:
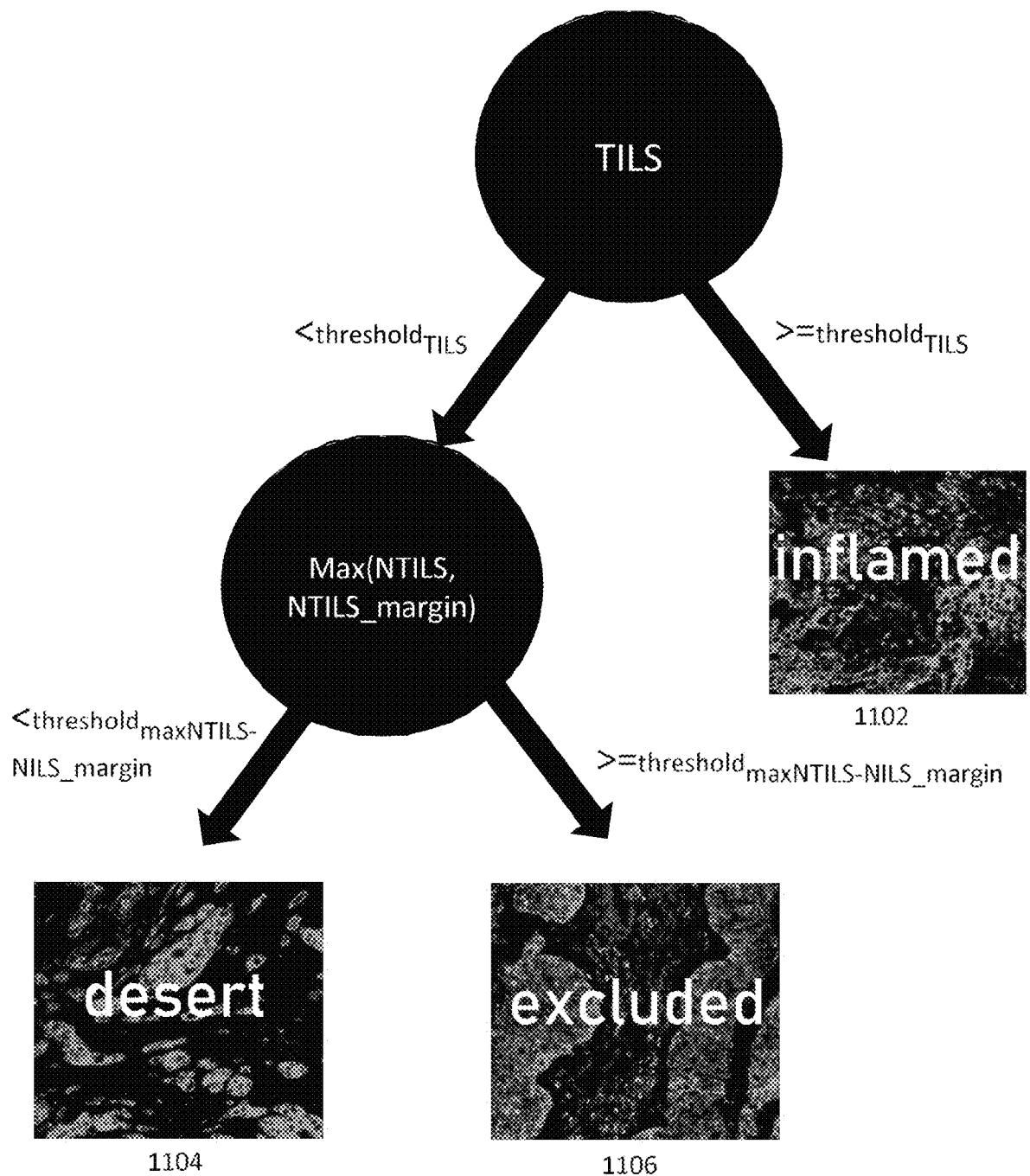
FIG. 11 schematically depicts a classification rule for classifying patients into one of three tumor-immune phenotypes in accordance with some embodiments of the present disclosure.

The computing device classifies the patient into one of three tumor-immune phenotypes based on the patient level TILS, the patient level NTILS, and the patient level NTILS_margin, a first threshold and a second threshold (228 of FIG. 2). FIG. 11 schematically depicts a phenotype classification rule that is employed in some embodiments. The computing device determines whether the TILS falls below a first threshold value, which may be referred to as a TILS threshold value herein. If the TILS meets or exceeds the TILS threshold value, the patient is classified into the inflamed tumor-immune phenotype 1102. If the TILS falls below the TILS threshold value, the computing device determines whether the larger of the NTILS or the NTILS_margin falls below a second threshold value, which may be referred to as the max NTILS-NTILS_margin threshold value. If the larger of the NTILS or the NTILS_margin falls below the max NTILS-NTILS_margin threshold value, the patient is classified into the immune desert phenotype 1104. If the larger of the NTILS or the NTILS_margin meets or exceeds the max NTILS-NTILS_margin threshold value and the TILS falls below the TILS threshold value, the patient is classified into the immune-excluded tumor-immune phenotype 1106.

In some embodiments, the TILS threshold value and/or the max NTILS-NTILS_margin threshold value may be applicable for different types of tumors (e.g., colorectal cancer, gastric cancer, bladder cancer, head and neck cancer, ovarian cancer, etc.). In some embodiments, the TILS threshold value and/or the max NTILS-NTILS_margin threshold value may be specific to a certain type of tumor or a certain family of tumors. In some embodiments, different thresholds may be used for different types of cancers.

In some embodiments, the TILS threshold value is 0.005 or about 0.005. In some embodiments, The TILS threshold value is in a range of 0.0045 to 0.0055 inclusive. In some embodiments, the TILS threshold value is in a range of 0.004 to 0.0006 inclusive. In some embodiments, the max NTILS-NTILS_margin threshold value is 0.0025 or about 0.0025. In some embodiments, the max NTILS-NTILS_margin threshold value is in a range of 0.002 to 0.003 inclusive. In some embodiments, the max NTILS-NTILS_margin threshold value is in a range of 0.0015 to 0.0035 inclusive. In some embodiments, one or both of the TILS threshold value and the max NTILS-NTILS_margin threshold value, may be in a range of 0.001 to 0.5 inclusive. In some embodiments, the TILS threshold value is in a range of 0.0045 to 0.0065 inclusive and NTILS-NTILS_margin threshold value is in a range of 0.0020 to 0.0030 inclusive.

In some embodiments, the TILS threshold value and the max NTILS-NTILS_margin threshold value are determined based on training data. For example, training data may be provided that includes a set of sample digital microscopy images of IF pathology slides associated with tumors for which a tumor-immune phenotype has already been determined by a pathologist and a tissue level tumor mask for each. The process with the training data is the same as the process described above up through calculation of the patient level TILS, NTILS, and NTILS_margin. At that point, the patient level TILS for the training data is used for determination of the TILS threshold value based on a receiver cooperating characteristic curve (ROC). The patient level NTILS and NTILS_margin is used for determination of the max NTILS-NTILS_margin threshold value based on another ROC curve. A separate testing data set can be used to assess the performance of the phenotype classification rule and the determined TILS and max NTILS-NTILS_margin threshold values.

In some embodiments, the TILS threshold and the max NTILS-NTILS_margin threshold values are determined based on training data including multiple different types of tumors (e.g., any of colorectal cancer, gastric cancer, bladder cancer, head and neck cancer, ovarian cancer, etc.). In some embodiments, the TILS threshold and the max NTILS-NTILS_margin threshold values are determined based on training data including only one type of cancer or only a family of cancers. Further details regarding training and determination of the TILS threshold value and the max NTILS-NTILS_margin threshold value are provided below with respect to the Example.

Exemplary Computing Device or System

Figure 12:
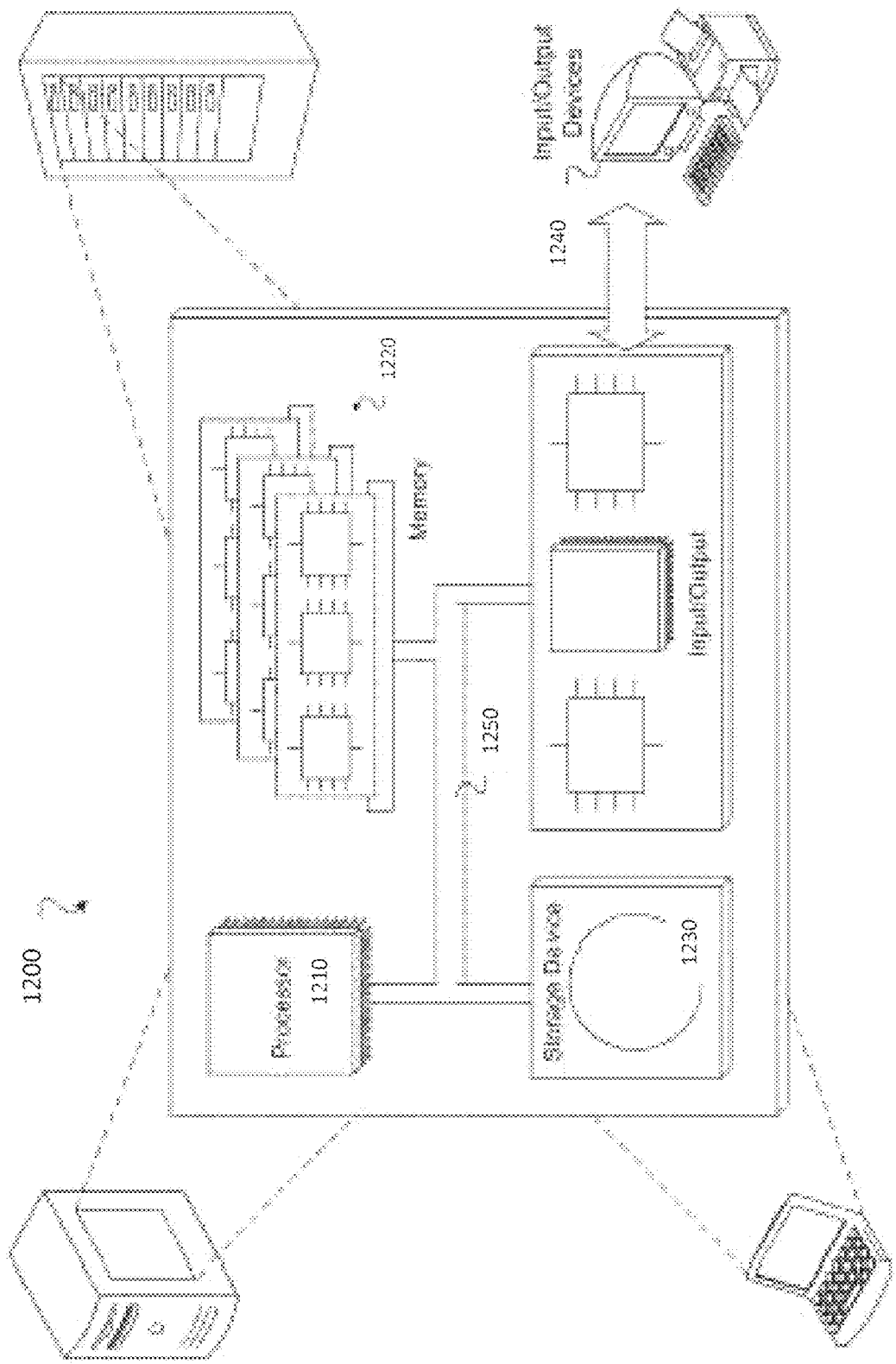
FIG. 12 schematically depicts an example computer system that can be used to execute some embodiments of the present disclosure.

FIG. 12 schematically depicts an exemplary computing device or system 1200 (e.g., the computing devices 102 or 108 in FIG. 1). The system 1200 may be used to perform the operations described with regard to one or more implementations according to any of the methods of the present disclosure. For example, the system 1200 may be included in any or all of the server components, or other computing device(s), discussed herein. The system 1200 may include one or more processors 1210, one or more memories 1220, one or more storage devices 1230, and one or more input/output (I/O) devices 1240. The components 1210, 1220, 1230, 1240 may be interconnected using a system bus 1250.

The processor 1210 may be configured to execute instructions within the system 1200. The processor 1210 may include a single-threaded processor or a multi-threaded processor. In some embodiments, the one or more processors 1200 may include one or more graphical processing units. The processor 1210 may be configured to execute or otherwise process instructions stored in one or both of the memory 1220 or the storage device 1230. Execution of the instruction(s) may cause graphical information to be displayed or otherwise presented via a user interface on the I/O device 1240. In some embodiments, the one or more processors may include one or more graphical processing units.

The memory 1220 may store information within the system 1200. In some implementations, the memory 1220 is a computer-readable medium. In some implementations, the memory 1220 may include one or more volatile memory units. In some implementations, the memory 1220 may include one or more non-volatile memory units.

The storage device 1230 may be configured to provide mass storage for the system 1200. In some implementations, the storage device 1230 is a computer-readable medium. The storage device 1230 may include a floppy disk device, a hard disk device, an optical disk device, a tape device, or other type of storage device. The I/O device 1240 may provide I/O operations for the system 1200. In some implementations, the I/O device 1240 may include a keyboard, a pointing device, or other devices for data input. In some implementations, the I/O device 1240 may include output devices such as a display unit for displaying graphical user interfaces or other types of user interfaces.

Example—Training and Testing of Tumor-Immune Phenotype Classification Across Multiple Tumor Types Training data was employed to determine a TILS threshold and a max NTILS-NTILS_margin threshold for tumor-immune phenotype classification and test data was employed to test the performance of the method described above for automated tumor-immune phenotype classification (e.g., immune desert, immune-excluded, or inflamed).

An initial data set included 103 digital microscopy images of IF pathology slides that was split into two sets: a training set of 68 including IF images for colorectal cancer, gastric cancer and bladder cancer, and a testing group of 35 including IF images for head and neck squamous cell carcinoma (HNSCC) and ovarian cancer. A tissue level tumor mask based on pathologist annotation was provided for each. In some embodiments, the annotation is performed by the pathologist using a hematoxylin-eosin (H&E) stained image.

Global thresholding was performed at the channel level for each microscopy image, also known as tissue level image, to determine a noise threshold for each channel (see FIG. 3). Each image was divided into a plurality of image tiles of 2500 pixels by 2500 pixels (corresponding to 125 microns by 125 microns) under 20× magnification (see FIG. 4). Separate color-based channel images were created from each tile to create biologically meaningful channels (see FIG. 5). In this example, the channels corresponded to epithelial cells marked by pan-CK, cell nuclei marked by DAPI, CD8+ lymphocytes, and CD3+ lymphocytes. The CD3+ lymphocyte channel was not used in the analysis, but was simply used for verification. Each color-based channel tile image employed the global threshold determined from the corresponding color-channel tissue level image to distinguish signal from noise.

Image morphology operations were performed on the color-channel based tile images. A kernel size of 75 pixels corresponding to about 3.75 microns, was used for the Top-Hat image morphology operation to correct-out-of-focus regions and staining artifacts for all channels. The Opening image morphology operation was used with a kernel size of 20 pixels (corresponding to about 1 micron) for the epithelial channel, and with a kernel size of 5 pixels (corresponding to about 0.25 micron) for the remaining channels to remove small artifacts. The Closing image morphology operation was used with a kernel size of 35 pixels (about 1.75 microns) to fill small holes for the epithelial channel, and with a kernel size of 10 pixels (about 0.5 microns) to fill small holes for the cell nuclei channel.

Each tile in the epithelial channel was segmented into a tumor region and a non-tumor region based on the tissue level tumor mask. A tumor margin region was determined for at least some of the tiles based on the tissue level tumor mask. The watershed image morphology operation was used to segment CD+ lymphocytes and a bounding box was generated for each segmented lymphocyte to locate the cell.

A total area of cell nuclei in the tile, a total area of the tile that is tumor region, a total area of the lymphocytes in the tumor region, a total area of the tile that is non-tumor region, a total area of the lymphocytes in the non-tumor region of the tile, and a total area of the tile that is tumor margin were calculated for the tiles.

Tile level TILS, NTILS, and NTILS_margin were calculated for tiles to be included in the aggregations for corresponding patient level TILS, NTILS, and NTILS_margin according to the equations above.

Aggregation filtering was applied to determine whether a tile would be included in the aggregation for the patient level scores. The aggregation filtering criteria for TILS aggregation was (1) greater than 1% of the tile area is cell nuclei, and (2) greater than 10% of the tile area is tumor region. The aggregation filtering criteria for NTILS aggregation was (1) greater than 1% of the tile area is cell nuclei, and (2) greater than a 1% of the tile area is non-tumor region. The aggregation filtering criteria for NTILS_margin aggregation was (1) greater than 40% of the tile area is tumor margin and (2) greater than 0.1% of the tile area is cell nuclei.

Patient level TILS, NTILS, and NTILS_margin were calculated based on the respective aggregated tiles as the median of the respective tile level TILS, NTILS, and NTILS_margin.

Figure 13A:
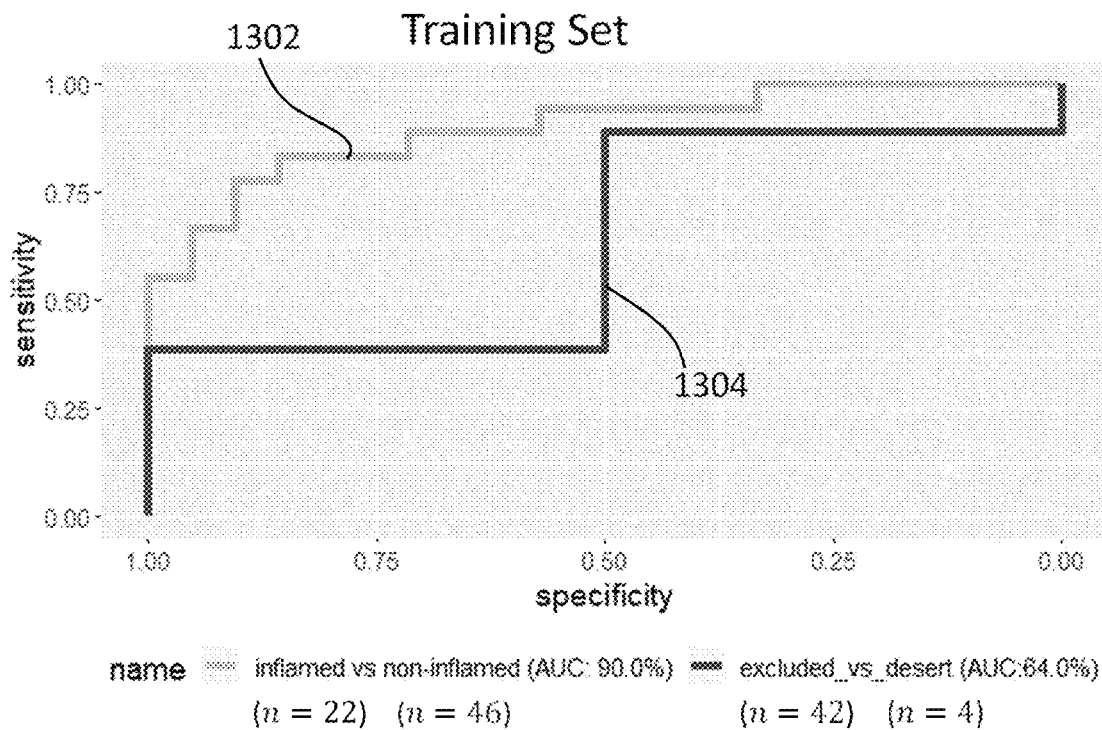
FIG. 13A is a graph of Receiver Operating Characteristic (ROC) curves for classification of inflamed versus noninflamed, and for classification of excluded versus desert for training data in an example.
Figure 13B:
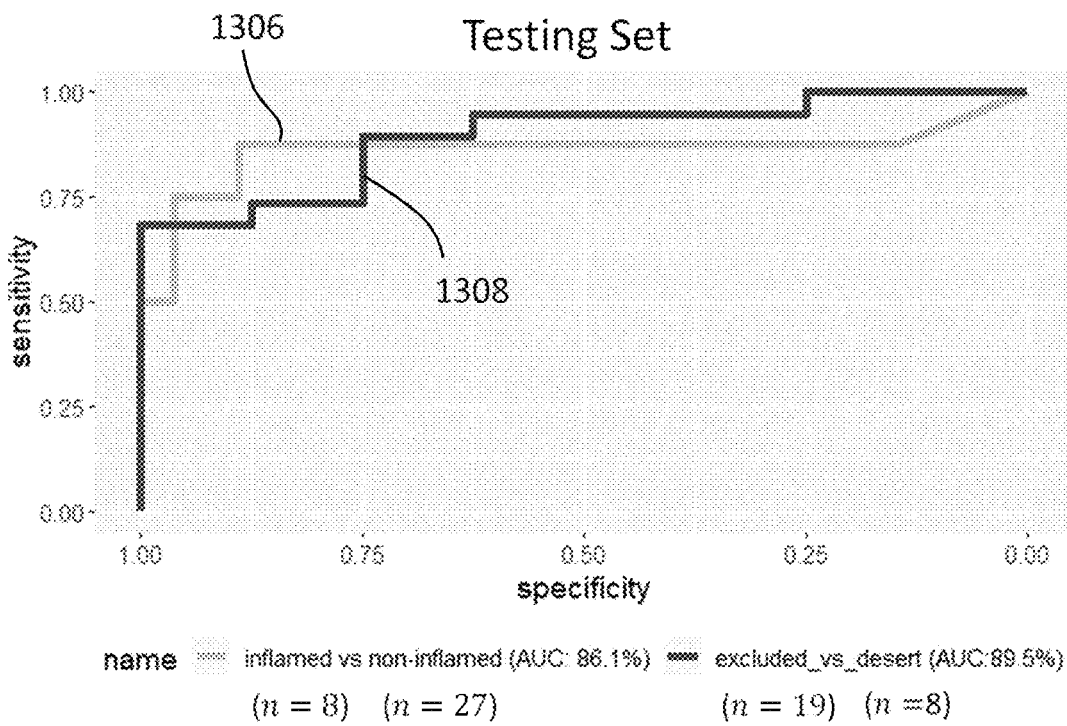
FIG. 13B is a graph of ROC curves for classification of inflamed versus noninflamed, and for classification of excluded versus desert for testing data in the example.
Figure 13C:
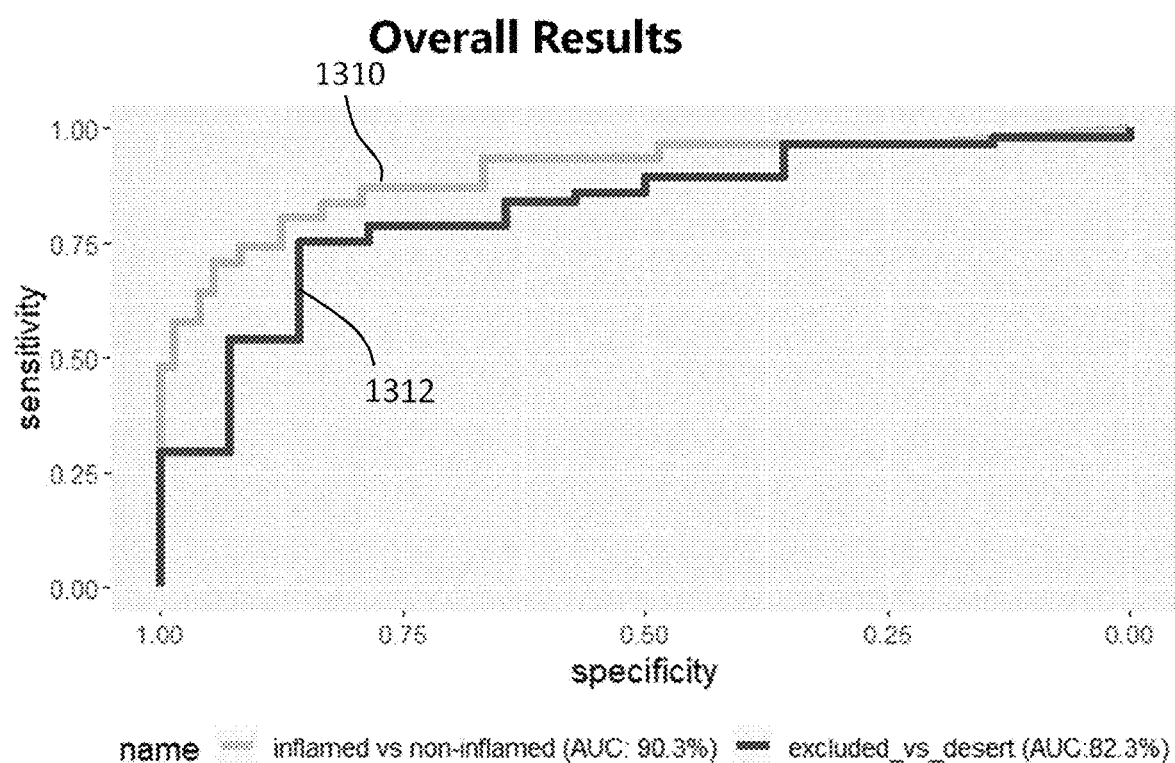
FIG. 13C is a graph of ROC curves for classification of inflamed versus noninflamed, and for classification of excluded versus desert for overall data including training data and testing data in the example.

The patient level TILS, NTILS, and NTILS_margin for the training data was used to determine the TILS threshold and the max NTILS-NTILS_margin threshold for the classification rule (see FIG. 11). The ROC was employed to determine the thresholds. These thresholds and the classification rule were then used to classify the test data. FIG. 13A is a graph of the ROC curves for the training set including inflamed versus noninflamed 1302, which is determined by the TILS threshold, and excluded versus desert 1304, which is determined by the mas NTILS-NTILS_margin threshold. In this training set, the number of desert samples was small leading to this less than ideal shape of the ROC curve for excluded versus desert. FIG. 13B is a graph of the ROC curves for the testing set including inflamed versus noninflamed 1306 and excluded versus desert 1308. The testing set had a larger number of desert samples and better illustrated the behavior of the ROC curve for excluded versus desert. The ROC curves in FIGS. 13A and 13B demonstrate the improvement in AUC from the training set to the testing set in correctly determining immune topography. Further, the ROC curves for the training set and the testing set show the generalizability of the method across different types of cancer in that the training set included different types of cancers than those included in the testing set. FIG. 13C is a graph of the ROC curves including inflamed versus noninflamed 1310 and excluded versus desert 1312 for an overall test set including both the training and the test set. The method and the classification rule showed a high level of generalizability without excessive overfitting.

A TILS threshold and a max NTILS-NTILS_margin threshold were selected for the classification rule. The tumor-immune phenotype classifications based on the example method were compared with pathologist tumor-immune phenotype classifications and classifications obtained using a third party algorithm that assumes that all epithelial cells are tumor with the results in the table below.

| | Concordance Between Pathologist Tumor-immune phenotype Classification and | (95% confidence interval) |
|---|---|---|
| Example Method | 74% | (58%, 90%) |
| Third Party Vendor Algorithm | 35% | (16%, 55%) |

The example method for immune phenotyping achieved a significantly higher degree of concordance with pathologists' tumor-immune phenotype classification compared to a third party algorithm. Using quantifiable TILS, NTILS, and NTILS_margin showed increased stratification between inflamed and excluded/desert phenotypes.

Embodiments described herein incorporate a practical application of automated identification of a patient tumor-immune phenotype from multiplex IF image analysis of pathology images. Some embodiments improve the efficiency of a computer or computing system by efficiently identifying image data corresponding to cancer cells and lymphocytes. Some embodiments improve the efficiency of a computer or computing system by performing some operations at a tile level only if those operations contribute to the overall scores used for classification (e.g., aggregation filtering for patient level TILS, NTILS, and NTILS_margin).

The features described may be implemented in digital electronic circuitry, or in computer hardware, firmware, software, or in combinations of them. The apparatus may be implemented in a computer program product tangibly embodied in an information carrier (e.g., in a machine-readable storage device) for execution by a programmable processor; and method steps may be performed by a programmable processor executing a program of instructions to perform functions of the described implementations by operating on input data and generating output. The described features may be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that may be used, directly or indirectly, in a computer to perform a certain activity or bring about a certain result. A computer program may be written in any form of programming language, including compiled or interpreted languages, and it may be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. Elements of a computer may include a processor for executing instructions and one or more memories for storing instructions and data. Generally, a computer may also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory may be supplemented by, or incorporated in, application-specific integrated circuits (ASICs).

To provide for interaction with a user, the features may be implemented on a computer having a display device such as a cathode ray tube (CRT) or liquid crystal display (LCD) monitor for displaying information to the user and a keyboard and a pointing device such as a mouse or a trackball by which the user may provide input to the computer.

The features may be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system may be connected by any form or medium of digital data communication such as a communication network. Examples of communication networks include, e.g., a local area network (LAN), a wide area network (WAN), and the computers and networks forming the Internet.

The computer system may include clients and servers. A client and server are generally remote from each other and typically interact through a network, such as the described one. The relationship of client and server arises by virtue of computer programs running on the respective computers and having a client-server relationship to each other.

In addition, the logic flows depicted in the figures do not require the particular order shown, or sequential order, to achieve desirable results. In addition, other steps may be provided, or steps may be eliminated, from the described flows, and other components may be added to, or removed from, the described systems. A number of implementations of the present disclosure have been described. Nevertheless, it will be understood that various modifications may be made without departing from the spirit and scope of the present disclosure. Accordingly, other implementations are within the scope of the following claims.

We claim:

1. A computer-implemented method executed by one or more processors for classifying a patient into a tumor-immune phenotype, the method comprising;
   receiving or obtaining, from one or more databases, at least one digital microscopy image of an immunofluorescence (IF) pathology slide of the patient;
   receiving or obtaining a tissue level tumor mask identifying which portion or portions of the at least one digital microscopy image correspond to one or more tumor nests;
   producing a plurality of color-based channel images each corresponding to a different color-based channel in a plurality of color-based channels for each tile in a plurality of tiles cumulatively corresponding to the at least one digital microscopy image of the IF pathology slide, wherein the plurality of color-based channels comprises an epithelial cell channel including epithelial cell image data, a cell nuclei channel including cell nuclei image data, and at least one lymphocyte channel including lymphocyte image data;
   for at least some of the tiles in the plurality of tiles, segmenting the epithelial cell image data for the tile into a tumor region and a non-tumor region based on the tissue level tumor mask and the epithelial cell image data;
   for at least some of the tiles in the plurality of tiles, determining a tumor margin region for the tile based on a pre-specified margin outside a boundary of the tumor region based on the tissue level tumor mask;
   for the tiles including lymphocyte image data, determining a location and an area for each lymphocyte within the tile;
   for at least some of the tiles in the plurality of tiles, calculating a tumor infiltrating lymphocytes score (TILS) based on a total area of the lymphocytes in the tumor region and a total area of the tumor region for the tile;
   for at least some of the tiles in the plurality of tiles, calculating a non-tumor infiltrating lymphocytes score (NTILS) based on a total area of the lymphocytes in the non-tumor region and a total area of the non-tumor region for the tile;
   for at least some of the tiles in the plurality of tiles, calculating a non-tumor infiltrating lymphocytes at tumor margin score (NTILS_Margin) based on a total area of lymphocytes in the tumor margin and a total area of the tumor margin for the tile;
   aggregating tile level results from at least some of the plurality of tiles to determine a patient level tumor infiltrating lymphocytes score, a patient level non-tumor infiltrating lymphocytes score, and a patient level non-tumor infiltrating lymphocytes at tumor margin score; and classifying the patient into a tumor-immune phenotype of a plurality of tumor-immune phenotypes including immune deserts, immune-excluded tumors and inflamed tumors based on the patient level tumor infiltrating lymphocytes score, the patient level non-tumor infiltrating lymphocytes score, and the patient level non-tumor infiltrating lymphocytes at the tumor margin score.

2. The method of claim 1, wherein classifying the patient into a tumor-immune phenotype of a plurality of tumor-immune phenotypes comprises:

comparing the patient level tumor infiltrating lymphocytes score to a first threshold;

where the patient level tumor infiltrating lymphocytes score meets or exceeds the first threshold, classifying the patient into an inflamed tumor-immune phenotype; and where the patient level tumor infiltrating lymphocytes score falls below the first threshold:

comparing the larger of the patient level non-tumor infiltrating lymphocytes score and the patient level non-tumor infiltrating lymphocytes at the tumor margin score to a second threshold;

where the larger of the patient level non-tumor infiltrating lymphocytes score and the patient level non-tumor infiltrating lymphocytes at the tumor margin score falls below the second threshold, classifying the patient into an immune desert phenotype; and where the larger of the patient level non-tumor infiltrating lymphocytes score and the patient level non-tumor infiltrating lymphocytes at the tumor margin score meets or exceeds the second threshold, classifying the patient into an immune-excluded tumor-immune phenotype.

3. The method of claim 2, wherein the first threshold is in a range of 0.0045 to 0.0055, or the second threshold is in a range of 0.0020 to 0.0030, or the first threshold is in a range of 0.0045 to 0.0055 and the second threshold is in a range of 0.0020 to 0.0030.

4. The method of claim 2, wherein the first threshold and the second threshold are determined based on training data.

5. The method of claim 2, wherein the first threshold and the second threshold were determined based on training data including multiple different types of cancer and the first threshold and the second threshold are applicable to multiple different types of cancer.

6. The method of claim 2, wherein the first threshold and the second threshold were determined based on training data including only one type of cancer and the first threshold and the second threshold are specific to a single type of cancer.

7. The method of claim 1, wherein producing the plurality of color-based channel images comprises dividing the at least one digital microscopy image of the IF pathology slide into a plurality of image tiles, and creating the plurality of color-based channel images for each of the plurality of image tiles from the corresponding image tile using color deconvolution.

8. The method of claim 1, wherein producing the plurality of color-based channel images comprises creating a plurality of full image, color-based channel images from the at least one digital microscopy image using color deconvolution, and dividing each of the plurality of full image, color-based channel images into tiles to form the plurality of color-based channel images for each of the plurality of image tiles.

9. The method of claim 1, wherein the tumor infiltrating lymphocytes score (TILS) for a tile is determined based on the total area of lymphocytes in the tumor region divided by the total area of the tumor region for the tile;

wherein the non-tumor infiltrating lymphocytes score (NTILS) for a tile is determined based the total area of lymphocytes in the non-tumor region for the tile divided by the total area of the non-tumor region for the tile; and wherein the non-tumor infiltrating lymphocytes at tumor margin score (NTILS_margin) for a tile is determined based the total area of lymphocytes in the tumor margin that is divided by the total area of the tumor margin for the tile.

10. The method of claim 1, wherein the at least one lymphocyte channel includes cytotoxic lymphocyte image data.

11. The method of claim 1, wherein the epithelial cell channel includes pan cytokeratin (pan-CK) stained marker image data, the cell nuclei channel includes 4',6-diamidino-2-phenylindole (DAPI) stained marker image data, or the epithelial cell channel includes pan cytokeratin (pan-CK) stained marker image data and the cell nuclei channel includes 4',6-diamidino-2-phenylindole (DAPI) stained marker image data.

12. The method of claim 1, wherein aggregating the tile level results includes:

aggregating tumor infiltrating lymphocytes scores for all the tiles of the plurality of tiles;

aggregating non-tumor infiltrating lymphocytes scores for all the tiles of the plurality of tiles; and aggregating non-tumor infiltrating lymphocytes at tumor margin scores for all the tiles of the plurality of tiles.

13. The method of claim 1, wherein for at least some of the plurality color-based channel images for at least some of the plurality of tiles, the method further comprises employing at least one image morphology filter to correct the color-based channel images.

14. The method of claim 1, wherein for at least some of the plurality color-based channel images for at least some of the plurality of tiles, the method further comprises using parallel graphics processing units (GPUs) to perform parallel image morphology operations to correct the color-based channel images.

15. The method of claim 1, further comprising:

for each tile in some or all of the plurality of tiles:

determining a total area of cell nuclei for the tile where the tile includes cell nuclei;

determining a total area of the tumor region for the tile where the tile includes tumor region;

determining a total area of lymphocytes in the tumor region for the tile where the tile includes tumor region;

determining a total area of the non-tumor region for the tile where the tile includes non-tumor region;

determining a total area of lymphocytes in the non-tumor region for the tile where the tile includes non-tumor region;

determining a total area of the tumor margin region for the tile where the tile includes tumor margin region; and determining a total area of nuclei in the tumor margin region for the tile where the tile includes tumor margin region; and for each tile in some or all of the plurality of tiles, performing one or more of:
    determining whether the tile is included in aggregated tile results for the patient level tumor infiltrating lymphocytes score based on whether the total area of cell nuclei for the tile meets a TILS minimum nuclei threshold and based on whether the total tumor region area meets a minimum tumor area threshold;
    determining whether the tile is included in aggregated tile results for the patient level non-tumor infiltrating lymphocytes score based on whether the total area of cell nuclei for the tile meets an NTILS minimum nuclei threshold and based on whether the total non-tumor region area meets a minimum non-tumor area threshold; and
    determining whether the tile is included in aggregated tile results for the patient level non-tumor infiltrating lymphocytes at tumor margin score based on whether the total tumor margin area meets minimum tumor margin area threshold and based on the total area of cell nuclei in the tumor margin for the tile meets a minimum tumor margin nuclei threshold.

16. The method of claim 15, wherein the patient level tumor infiltrating lymphocytes score is the median of the tile level tumor infiltrating lymphocytes scores for the tiles included in the aggregated tile level results for the tumor infiltrating lymphocytes score;
    wherein the patient level non-tumor infiltrating lymphocytes score is the median of the tile level non-tumor infiltrating lymphocytes scores for the tiles included in the aggregated tile level results for the non-tumor infiltrating lymphocytes score; and
    wherein the patient level non-tumor infiltrating lymphocytes at the tumor margin score is the median of the tile level non-tumor infiltrating lymphocytes at the tumor margin scores for the tiles included in the aggregated tile level results for the non-tumor infiltrating lymphocytes at the tumor margin score.

17. A system for determining a tumor-immune phenotype of a patient, the system comprising:
    one or more databases; and
    one or more processors configured to:
        receive or obtain, from the one or more databases, at least one digital microscopy image of an immunofluorescence (IF) pathology slide of the patient;
        receive or obtain a tissue level tumor mask identifying which portion or portions of the digital microscopy image correspond to one or more tumor nests;
        produce a plurality of color-based channel images each corresponding to a different color-based channel in a plurality of color-based channels for each image tile in a plurality of image tiles cumulatively corresponding to the at least one digital microscopy image of the IF pathology slide, wherein the plurality of color-based channels comprises: an epithelial channel including epithelial cell image data, a nuclei channel including nuclei image data, and at least one lymphocyte channel including lymphocyte image data;
        for at least some of the tiles in the plurality of tiles, segment the epithelial channel image for the tile into a tumor region and a non-tumor region based on the tissue level tumor mask and the epithelial cell image data;
        for at least some of the tiles in the plurality of tiles, determine a tumor margin region for the tile based on a pre-specified margin outside a boundary of the tumor region based on the tissue level tumor mask;
        for the tiles including lymphocyte image data, determine a location and an area for each lymphocyte within the tile;
        for at least some of the tiles in the plurality of tiles, calculate a tumor infiltrating lymphocytes score (TILS) based on a total area of the lymphocytes in the tumor region and a total area of the tumor region for the tile;
        for at least some of the tiles in the plurality of tiles, calculate a non-tumor infiltrating lymphocytes score (NTILS) based on a total area of the lymphocytes in the non-tumor region and a total area of the non-tumor region for the tile;
        for at least some of the tiles in the plurality of tiles, calculate a non-tumor infiltrating lymphocytes at tumor margin score (NTILS_Margin) based on a total area of lymphocytes in the tumor margin and a total area of the tumor margin for the tile;
        aggregate tile level results from at least some of the plurality of tiles to determine a patient level tumor infiltrating lymphocytes score, a patient level non-tumor infiltrating lymphocytes score, and a patient level non-tumor infiltrating lymphocytes at tumor margin score; and
        classify the patient into a tumor-immune phenotype of a plurality of tumor-immune phenotypes including immune deserts, immune-excluded tumors and inflamed tumors based on the patient level tumor infiltrating lymphocytes score, the patient level non-tumor infiltrating lymphocytes score, and the patient level non-tumor infiltrating lymphocytes at the tumor margin score.

18. The system of claim 17, wherein the one or more processors are configured to classify the patient into a tumor-immune phenotype of a plurality of tumor-immune phenotypes by:
    comparing the patient level tumor infiltrating lymphocytes score to a first threshold;
    where the patient level tumor infiltrating lymphocytes score meets or exceeds the first threshold, classifying the patient into an inflamed tumor-immune phenotype; and
    where the patient level tumor infiltrating lymphocytes score falls below the first threshold:
        comparing the larger of the patient level non-tumor infiltrating lymphocytes score and the patient level non-tumor infiltrating lymphocytes at the tumor margin score to a second threshold;
        where the larger of the patient level non-tumor infiltrating lymphocytes score and the patient level non-tumor infiltrating lymphocytes at the tumor margin score falls below the second threshold, classifying the patient into an immune desert phenotype; and
        where the larger of the patient level non-tumor infiltrating lymphocytes score and the patient level non-tumor infiltrating lymphocytes at the tumor margin score meets or exceeds the second threshold, classifying the patient into an immune-excluded tumor-immune phenotype.

19. The system of claim 17, wherein the instructions when executed on the one or more processors are configured to:
    determine the tumor infiltrating lymphocytes score (TILS) for a tile based on the total area of lymphocytes in the tumor region divided by the total area of the tumor region for the tile;
    determine the non-tumor infiltrating lymphocytes score (NTILS) for a tile based the total area of lymphocytes in the non-tumor region for the tile divided by the total area of the non-tumor region for the tile; and determine the non-tumor infiltrating lymphocytes at tumor margin score (NTILS_margin) for a tile based the total area of lymphocytes in the tumor margin that is divided by the total area of the tumor margin for the tile.

20. The system of claim 17, wherein the one or more processors are further configured to:

for each tile of some or all of the plurality of tiles:
    determine a total area of cell nuclei for the tile where the tile includes cell nuclei;
    determine a total area of the tumor region for the tile where the tile includes tumor region;
    determine a total area of lymphocytes in the tumor region for the tile where the tile includes tumor region;
    determine a total area of the non-tumor region for the tile where the tile includes non-tumor region;
    determine a total area of lymphocytes in the non-tumor region for the tile where the tile includes non-tumor region;
    determine a total area of the tumor margin region for the tile where the tile includes tumor margin region; and
    determine a total area of nuclei in the tumor margin region for the tile where the tile includes tumor margin region; and for each tile in some or all of the plurality of tiles, perform one or more of:
    determine whether the tile is included in the aggregated tile results for patient level tumor infiltrating lymphocytes score based on whether the total area of cell nuclei for the tile meets a TILS minimum nuclei threshold and based on whether the total tumor region area meets a minimum tumor area threshold;
    determine whether the tile is included in the aggregated tile results for patient level non-tumor infiltrating lymphocytes score based on whether the total area of cell nuclei for the tile meets an NTILS minimum nuclei threshold and based on whether the total non-tumor region area meets a minimum non-tumor area threshold; and
    determine whether the tile is included in the aggregated tile results for patient level a non-tumor infiltrating lymphocytes at tumor margin score based on whether the total tumor margin area meets minimum tumor margin area threshold and based on the total area of cell nuclei in the tumor margin for the tile meets a minimum tumor margin nuclei threshold.

21. The system of claim 20, wherein the patient level tumor infiltrating lymphocytes score is the median of the tile level tumor infiltrating lymphocytes scores for the tiles included in the aggregated tile level results for the tumor infiltrating lymphocytes score;

wherein the patient level non-tumor infiltrating lymphocytes score is the median of the tile level non-tumor infiltrating lymphocytes scores for the tiles included in the aggregated tile level results for the non-tumor infiltrating lymphocytes score; and wherein the patient level non-tumor infiltrating lymphocytes at the tumor margin score is the median of the tile level non-tumor infiltrating lymphocytes at the tumor margin scores for the tiles included in the aggregated tile level results for the non-tumor infiltrating lymphocytes at the tumor margin score.

* * * * *

UNITED STATES PATENT AND TRADEMARK OFFICE
CERTIFICATE OF CORRECTION

PATENT NO. : 12,141,971 B2
APPLICATION NO. : 17/722263
DATED : November 12, 2024
INVENTOR(S) : Caron et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 390 days.

Signed and Sealed this
Twentieth Day of May, 2025

Coke Morgan Stewart
*Acting Director of the United States Patent and Trademark Office*